United States Patent [19]

Danishefsky et al.

[11] Patent Number: 5,391,745
[45] Date of Patent: Feb. 21, 1995

[54] METHODS OF PREPARATION OF CAMPTOTHECIN ANALOGS

[75] Inventors: Samuel J. Danishefsky, New Haven, Conn.; William G. Bornmann; Wang Shen; Craig A. Coburn, all of New York, N.Y.

[73] Assignee: Sloan-Kettering Institute for Cancer Research, New York, N.Y.

[21] Appl. No.: 2,996

[22] Filed: Jan. 11, 1993

Related U.S. Application Data

[63] Continuation-in-part of Ser. No. 919,188, Jul. 23, 1992.

[51] Int. Cl.$^6$ ............... C07D 491/52; C07D 491/147
[52] U.S. Cl. .......................... 546/48; 546/92
[58] Field of Search ................... 546/48, 92

[56] References Cited

U.S. PATENT DOCUMENTS

| | | | |
|---|---|---|---|
| 3,894,029 | 7/1975 | Winterfeldt et al. | 260/287 R |
| 4,031,098 | 6/1977 | Sugasawa | 260/287 C |
| 4,399,282 | 8/1983 | Miyasaka et al. | 546/48 |
| 4,473,692 | 9/1984 | Miyasaka et al. | 546/48 |
| 4,513,138 | 4/1985 | Miyasaka et al. | 546/48 |
| 4,545,880 | 10/1985 | Miyasaka et al. | 204/158 |
| 4,604,463 | 8/1986 | Miyasaka et al. | 544/125 |
| 4,894,456 | 1/1990 | Wall et al. | 546/41 |
| 4,914,205 | 4/1990 | Sawada et al. | 546/70 |
| 4,939,255 | 7/1990 | Tagawa et al. | 540/578 |
| 4,943,579 | 7/1990 | Vishnuvajjala et al. | 514/283 |
| 4,981,968 | 1/1991 | Wall et al. | 544/361 |
| 5,004,758 | 4/1991 | Boehm et al. | 514/283 |
| 5,049,668 | 9/1991 | Wall et al. | 540/481 |
| 5,061,795 | 10/1991 | Tagawa et al. | 540/578 |
| 5,061,800 | 10/1991 | Yaegashi et al. | 546/48 |
| 5,106,742 | 4/1992 | Wall et al. | 435/233 |
| 5,122,526 | 6/1992 | Wall et al. | 514/253 |

OTHER PUBLICATIONS

Danishefsky, S., and Etheredge, S. J., Synthesis And Biological Evaluation of De-AB Camptothecin, *J. Org. Chem.*, 39:3430–3432 (1974).

Giovanella, B. C., et al., DNA Topoisomerase I-Targeted Chemotherapy of Human Colon Cancer in Xenografts, *Science*, 246:1046–1048 (1989).

(List continued on next page.)

Primary Examiner—Bernard Dentz
Attorney, Agent, or Firm—John P. White

[57] ABSTRACT

Substituted analoguss of camptothecin possessing cytotoxic activity towards cancer cells, of the general structure:

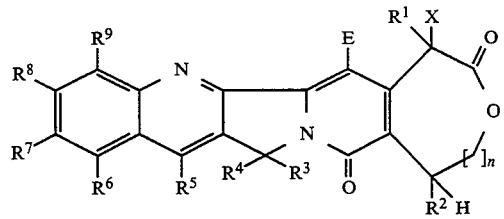

wherein E is H, $CO_2R$, $CONH_2$, $CONHR$, $CONR_2$, acyl, or CN; X is H OH, or OR; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or a C-glycal, or $CO_2R$, nitro, cyano, Cl, F, Br, I, $SR^{10}$, $NR^{11}R^{12}$, or $OR^{13}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, hydroxyalkyl, or acyl group, or an aryl group; $R^{13}$ is glycosyl; n is 0 or 1; with the proviso that when $R^1$ is ethyl, and n is 0, E, $R^2$, $R^3$, and $R^4$ are not all H. Intermediate compounds leading to the camptothecin analogues comprise substituted tricyclic compounds which consist of rings C, D, and E fused together. Methods for preparing the analoguss involve condensation of such intermediates with variably substituted protected α-aminobenzaldehydes.

11 Claims, 10 Drawing Sheets

OTHER PUBLICATIONS

Hsiang, Y.-H., et al., Camptothecin Induces Protein-linked DNA Breaks Via Mammalian DNA Topoisomerase I, *J. Biol. Chem.*, 260:14873–14878 (1985).

Hsiang, Y.-H., and Liu, L. F., Identification of Mammalian DNA Topoisomerase I as An Intracellular Target Of The Anticancer Drug Camptothecin, *Cancer Research*, 48:1722–1726 (1988).

T. Kunimoto, et al., Antitumor Activity of 7-Ethyl-10-[4-(1-piperidine)-1-piperidine]-carbonyloxy-camptothecin, A Novel Water-soluble Derivative of Camptothecin, Against Murine Tumors, *Cancer Research*, 47:5944–5947 (1987).

FIGURE 1B a. Dimethyl sulfate
b. Meldrum's acid, triethylamine, benzene
c. Sodium methoxide, methanol
d. Dimethyl allene-1,3-dicarboxylate, triethylamine
e. Potassium t-butoxide, THF, Ethyl iodide
f. Formaldehyde, acid
g. Hydrobromic acid, reflux
h. Selenium dioxide, 160°C, dioxane
i. Pyridinium dichromate, 0°C
j. o-Aminophenyl toluidine, toluene, tosic acid

FIGURE 2B k. Selenium dioxide, 160°C, dioxane
l. Pyridinium dichromate, 0°C
m. o-Aminophenyl toluidine, toluene, tosic acid

FIGURE 3B a. Davis' oxaziridine, KHMDS, THF
b. Pyridinium dichromate, 0°C
c. o-Aminophenyl toluidine, toluene, tosic acid
d. Hydrobromic acid, reflux
e. $CuCl_2$, oxygen, dimethylamine, DMF

FIGURE 4B a. Davis' oxaziridine, KHMDS, THF
b. Pyridinium dichromate, 0°C
c. o-Aminophenyl toluidine, toluene, tosic acid
d. $CuCl_2$, oxygen, dimethylamine, DMF

METHODS OF PREPARATION OF CAMPTOTHECIN ANALOGS

This application is a continuation-in-part of U.S. Ser. No. 07/919,188, filed Jul. 23, 1992, the contents of which are hereby incorporated by reference into this application.

BACKGROUND OF THE INVENTION

This invention relates to new camptothecin analogues useful for the treatment of cancer, to intermediates useful for their synthesis, and to methods of preparing the analogues and intermediates.

Camptothecin (1) is a pentacyclic alkaloid possessing a fused quinoline in rings A and B, a pyrroline in ring C, an α-pyridone in ring D, and a six-membered lactone in ring E, and was first isolated from *Camptotheca acuminata* (Nyssaceae), a tree native to southern China (Wall, et al., *J. Amer. Chem. Soc.*, 88, 3888–3890 (1966)). Promising antitumor and antileukemic activity and extreme rarity of the compound in nature (present in stem bark at abundances of about 0.01% by weight) have motivated extensive studies directed toward the total synthesis of camptothecin as well as the design of analogues intended to exhibit greater activity and lower toxicity than camptothecin itself. The results of these efforts have been comprehensively reviewed (C. R. Hutchinson, *Tetrahedron*, 37, 1047–1065 (1981); A. G. Schultz, *Chemical Rev.*, 73, 385–405 (1973)).

Mechanistic studies of the biological action of camptothecin have pointed to the enzyme topoisomerase I as the main intracellular target of the compound. By binding to and stabilizing a covalent DNA-topoisomerase I complex in which a strand of DNA is broken (R. P. Hertzberg, et al., *J. Med. Chem.*, 32, 715 (1989); W. D. Kingsbury, et al., *J. Med. Chem.*, 34, 98 (1991)), it is believed, camptothecin damages DNA and strongly inhibits the synthesis of nucleic acids in cancer cells. A structure-activity correlation for camptothecin analogues has been established between the anti-cancer activity of an analogue and its ability to stabilize the DNA-topoisomerase I complex. Adding further weight to this belief, cell lines which are resistant to camptothecin have been determined to contain a mutated form of topoisomerase I (R. S. Gupta, et al., *Cancer Res.*, 48, 6404 (1988)).

High toxicity and low solubility have diminished the clinical utility of camptothecin, stimulating a search for derivatives which transcend these limitations. Numerous analogues have been prepared by methods described in previous disclosures. None of these methods, however, offer a general approach for preparing camptothecin analogues with highly variable ring substitution patterns. For example, Miyasaka, et al. (U.S. Pat. No. 4,399,282, issued Aug. 16, 1982), disclose camptothecin analogues substituted by an alkyl, aralkyl, alkoxycarbonyl, or alkoxyalkyl group exclusively in the 7-position, while J. C. Boehm, et al. (U.S. Pat. No. 5,004,758, issued Apr. 2, 1991), disclose camptothecins substituted at positions 9 and 10, and Miyasaka, et al. (U.S. Pat. no. 4,473,692, issued Sep. 25, 1984) provide compounds with certain groups located at positions 5, 7, and 10, but not otherwise. Because of the sparing solubility of camptothecin in many organic solvents, and because of the special characteristic of camptothecin that the aromatic rings lack sufficient reactivity to afford ring-substituted analogues, the usual electrophilic ring substitution reactions cannot be performed productively on the parent structure. As a result, few direct methods exist for the preparation of potentially valuable substitution patterns. In one exceptional instance, nitration has been effected by Chinese workers (P. Peichuang, et al., *Hau Hsueh Hsueh Pao*, 33, 71 (1975); *Chem. Abstr.*, 84, 115629p (1975)) at the 12-position under severe conditions (nitric acid/sulfuric acid) at the 9-position of a 10,11-methylenedioxycamptothecin (M. E. Wall, et al., U.S. Pat. No. 5,049,668, issued Sep. 17, 1991), and at the 10-position by proceeding through a tetrahydrocamptothecin intermediate followed by subsequent re-oxidation (Miyasaka, et al., U.S. Pat. No. 4,473,692, issued Aug. 25, 1984), thereby allowing access to a range of substitution but at the cost of starting from the rare native camptothecin or its analogues.

Chemical modifications of the A, B, or C rings are of greatest therapeutic interest based on previous structure-function studies. However, while most alterations in the D and E rings have resulted in depressed biological activity, certain modifications of these rings have been achieved without losing activity, as disclosed in U.S. Pat. No. 3,894,029, issued Jul. 18, 1975, U.S. Pat. No. 4,031,098, issued Jun. 21, 1977, U.S. Pat. No. 4,914,205, issued Apr. 3, 1990, and U.S. Pat. No. 4,943,579, issued Jul. 24, 1990. The present invention allows simultaneous substitution changes in all rings of camptothecin.

While several syntheses of camptothecin have been disclosed in prior art (for example, E. J. Corey, et al., *J. Amer. Chem. Soc.*, 40, 2140 (1975); J. C. Bradley, et al., *J. Org. Chem.*, 41, 699 (1976); G. Stork, et al., *J. Amer. Chem. Soc.*, 93, 4074 (1971); E. Winterfeld, et al., *Angew. Chem.*, 84, 265 (1972)), the present approach offers the combined advantages of good preparative yield. a minimum number of reaction steps, and synthetic flexibility in the design of derivative analogues of camptothecin. Certain embodiments of the present invention allow synthetic yields of camptothecin as high as 39% from abundantly available tricyclic pyridones. Because of the possibility of obtaining a large variety of analogues, and given the intense anti-cancer activity of the parent structure, the present invention makes feasible the large-scale synthesis of a many new anti-cancer pharmaceuticals with more desirable chemical and clinical properties. Valuable enhancements in properties include improved solubility, bioavailability, and anticancer activity. The present invention therefore provides methods which represent a potentially significant advance for cancer chemotherapy.

BRIEF DESCRIPTION OF THE FIGURES

A more complete understanding of the invention and many of its advantages will become apparent by reference to the detailed description which follows when considered in conjunction with the accompanying figures, wherein:

FIGS. 1A and 1B illustrate the preparation of native camptothecin via decarboxylation and $SeO_2$-mediated oxygenation and of a de-AB-camptothecin intermediate, according to the process of the subject invention.

FIGS. 2A and 2B provide the synthesis of 14-carbomethoxy-substituted dl-camptothecin via $SeO_2$-mediated oxygentation of a de-AB-camptothecin intermediate, according to the process of the subject invention.

FIGS. 3A and 3B show the preparation of native camptothecin via decarboxylation and Davis' oxaziridine-mediated oxygenation and of a 14-carbomethoxy-substituted de-AB-camptothecin intermediate, according to the process of the subject the invention.

FIGS. 4A and 4B exemplify the synthesis of 14-carbomethoxy-substituted camptothecin analogues via Davis' oxaziridine-mediated oxygenation of a de-AB-camptothecin intermediate, according to the process of the subject invention.

SUMMARY OF THE INVENTION

Figure 1A:
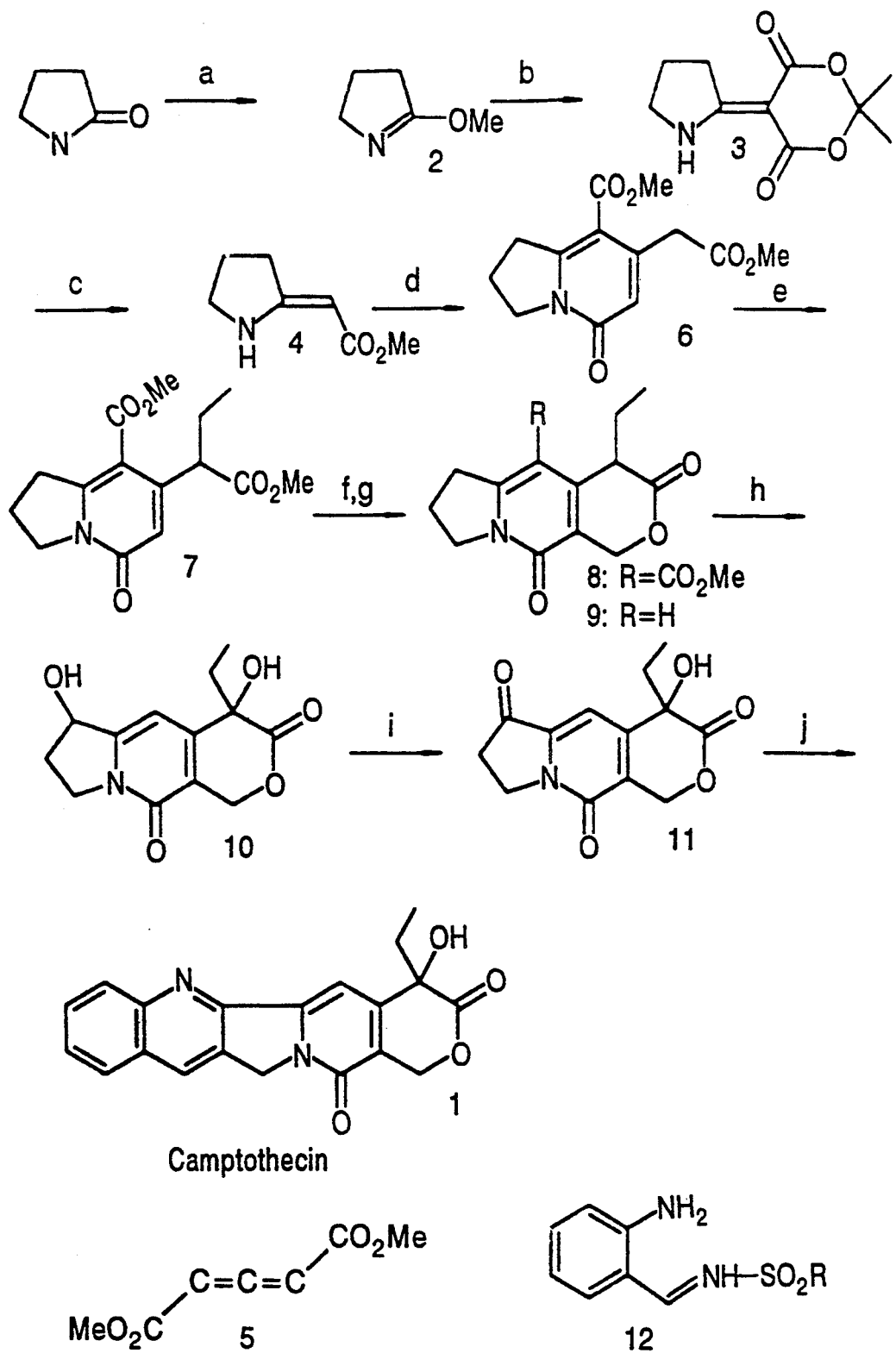
Figure 2A:
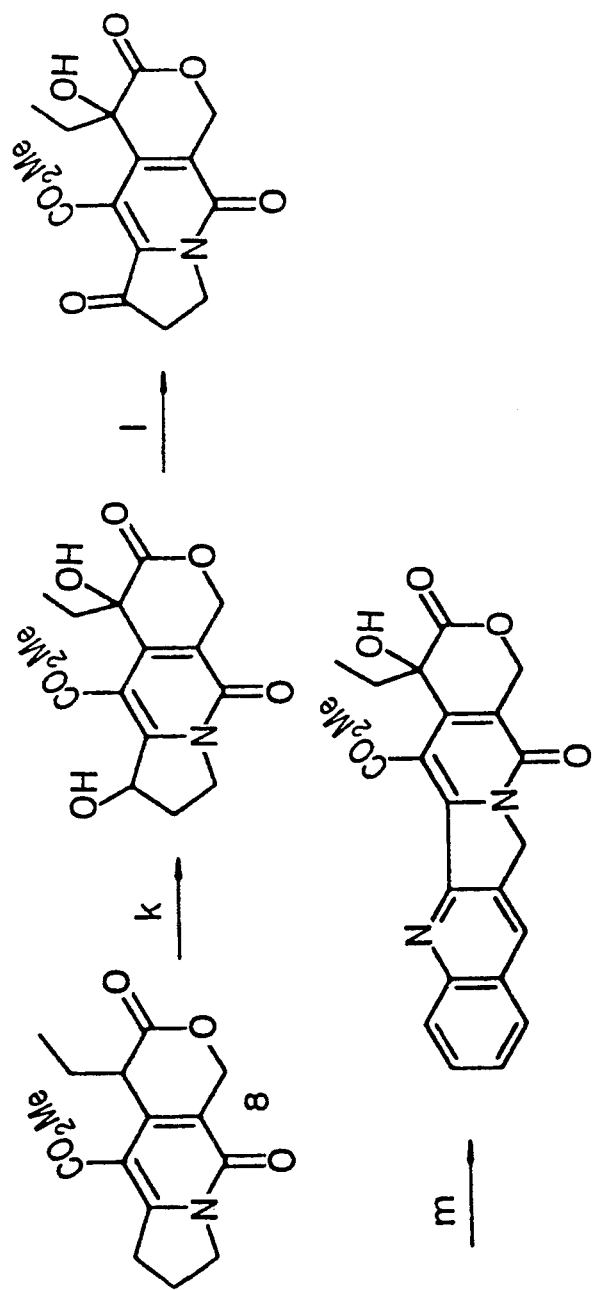
Figure 3A:
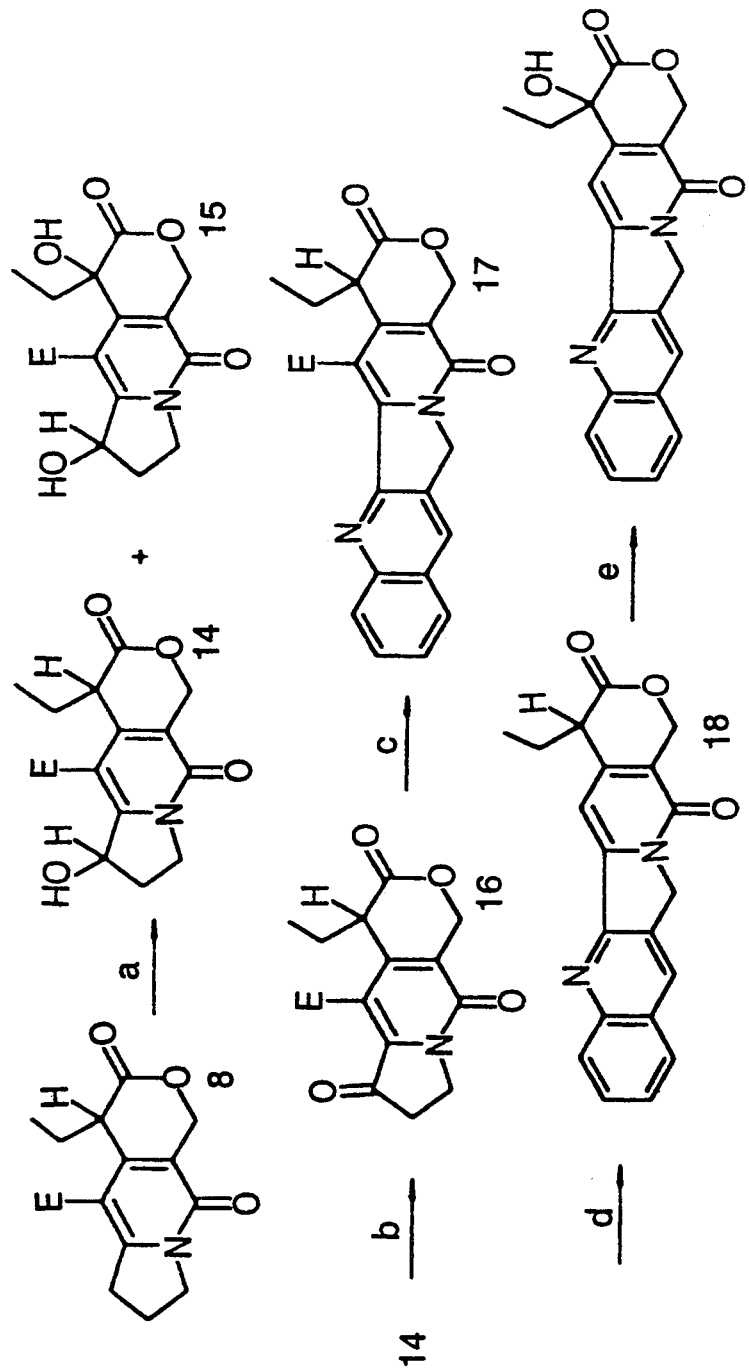
Figure 4A:
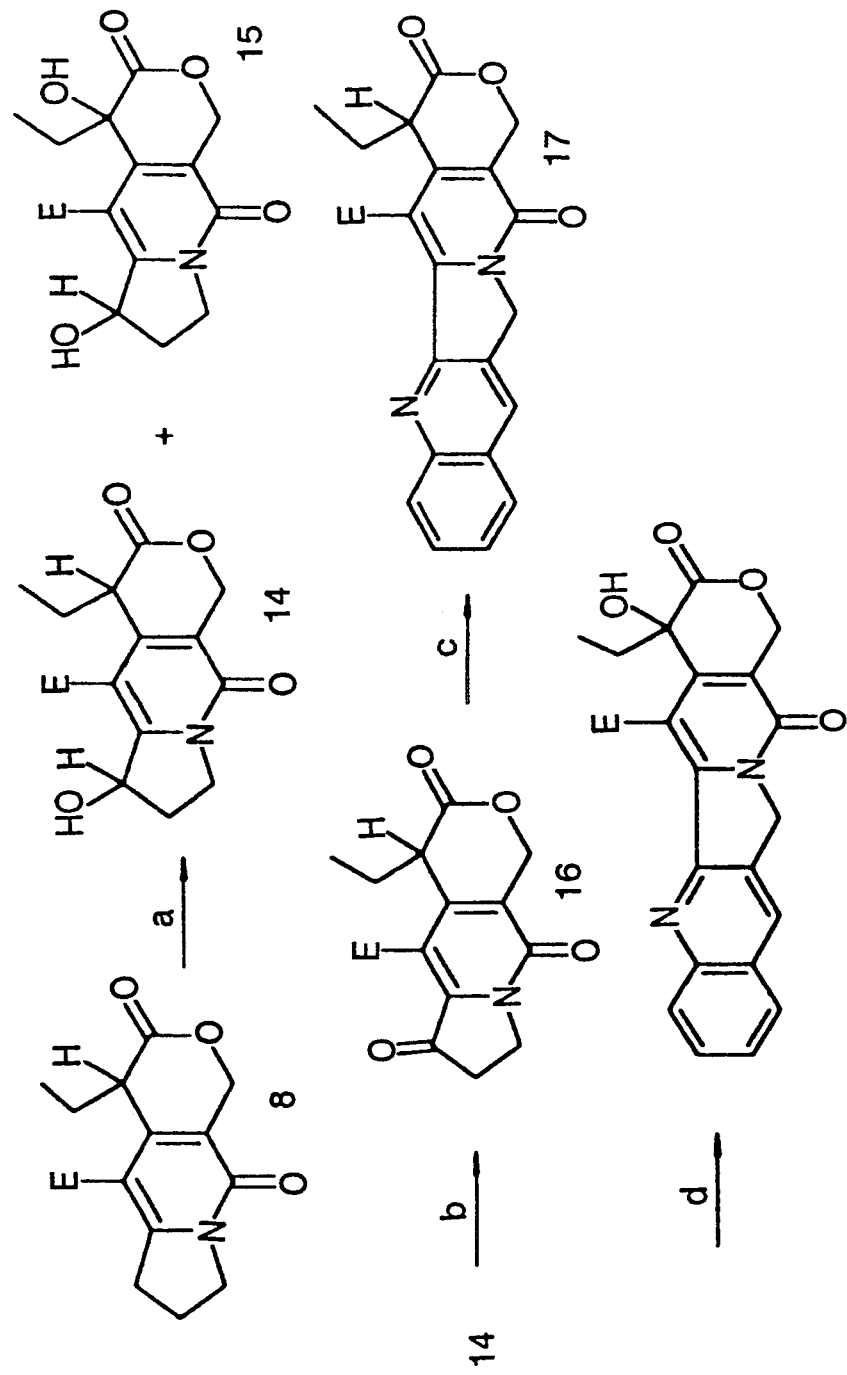
Figure 5:
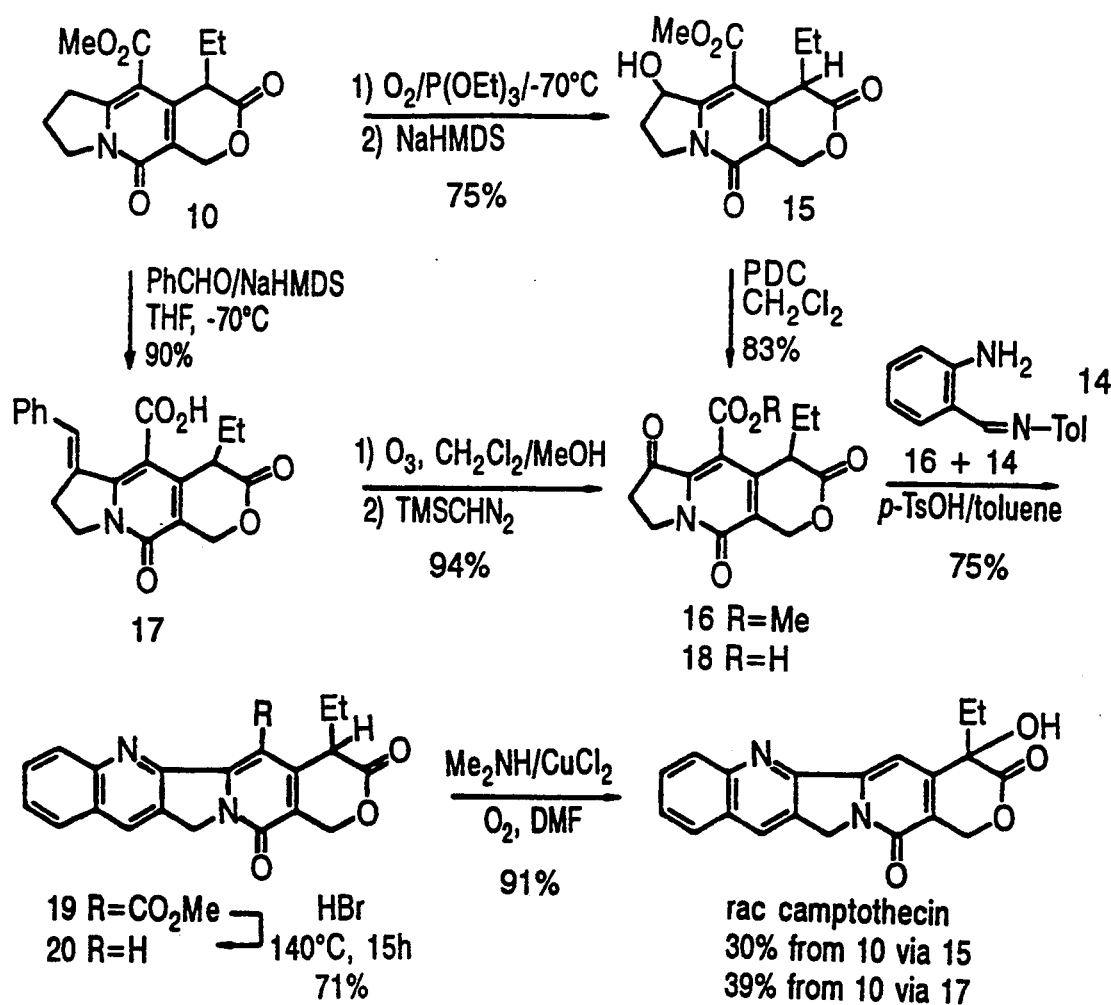
FIG. 5 illustrates the preparation of native camptothecin via a benzylidene or ketotricyclic intermediate, according to the process of the subject invention.
Figure 6:
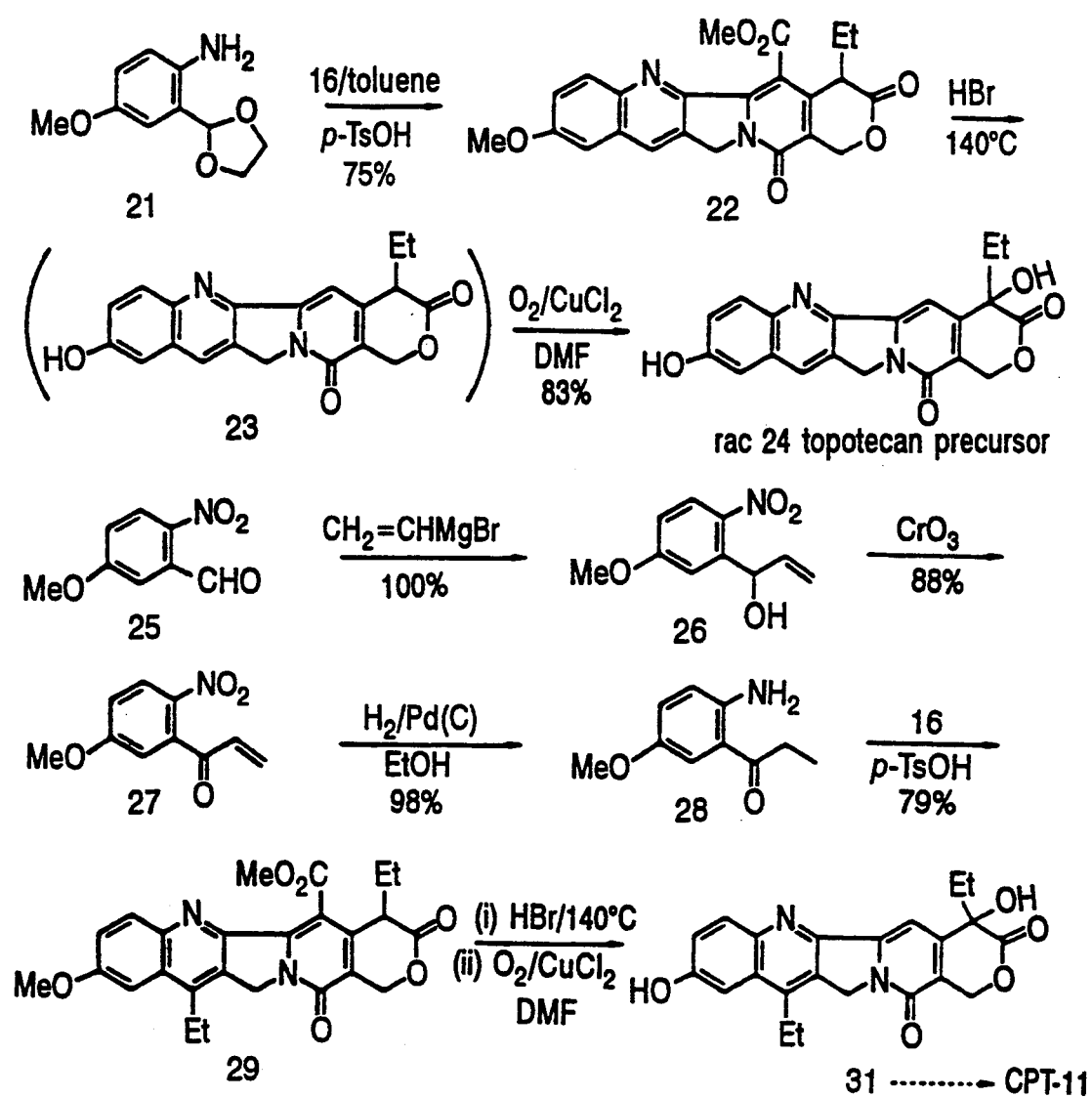
FIG. 6 illustrates the synthesis of a topotecan precursor and 10-hydroxycamptothecin derivatives via a vinyl Grignard aldol intermediate, according to the process of the subject invention.

The present invention relates to new substituted analogues of camptothecin bearing one or more groups in the 5-, 7-, 10-, 11-, 12-, 14-, 17- and/or 20-position thereof, and to methods of preparation of camptothecin and new analogues thereof.

Thus, the present invention provides a compound having the structure:

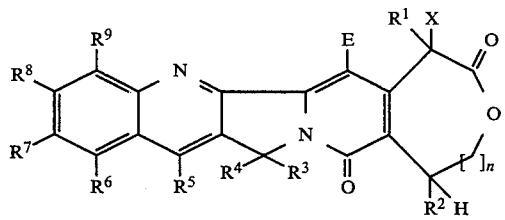

wherein E is H, $CO_2R$, $CONH_2$, CONHR, $CONR_2$, acyl, or CN; X, $R^1$ is O, or X is H or OH and $R^1$ is H, or a linear or branched chain alkyl, alkylaryl, or hydroxyalkyl group, or an aryl group; $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or a C-glycal, or $CO_2R$, nitro, cyano, Cl, F, Br, I, $SR^{10}$, or $NR^{11}R^{12}$, or $OR^{13}$; R is H, or a linear or branched chain alkyl, alkylaryl, or hydroxyalkyl group, or an aryl group; $R^{10}$, $R^{11}$ and $R^{12}$ are independently the same or different and are H, alkyl, aryl, alkylaryl, or acyl; $R^{13}$ is glycosyl; n is 0 or 1; with the proviso that when $R^1$ is ethyl, and n is 0, E, $R^2$, $R^3$ and $R^4$ are not all H. Another object of the invention is to provide key intermediates useful for the preparation of such new analogues of camptothecin.

Thus, the invention also provides a compound having the structure:

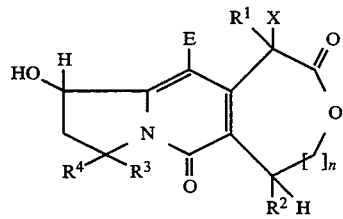

wherein E is H, $CO_2R$, $CONH_2$, CONHR, $CONR_2$, acyl, or CN; X is H, OH, or OR; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, with the proviso that when $R^1$ is ethyl, and n is 0, E, $R^2$, $R^3$, and $R^4$ are not all H.

The invention further provides a compound having the structure:

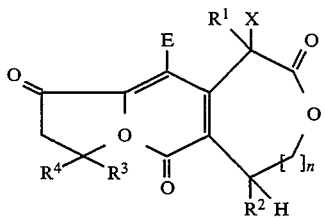

wherein E is H, $CO_2R$, $CONH_2$, CONHR, $CONR_2$, acyl, or CN; X is H, OH, or OR; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, with the proviso that when $R^1$ is ethyl, and n is 0, E, $R^2$, $R^3$, and $R^4$ are not all H.

An object of the present invention is to provide a process of synthesizing a compound having the structure:

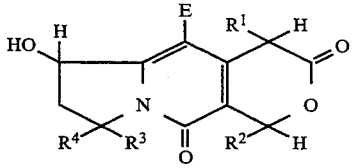

wherein E is H; X is OH; $R^1$, $R^2$, $R^3$, and $R^4$ are independently the same or different and are H, or a linear or branched chain alkyl, alkylaryl, or hydroxyalkyl group, or an aryl group; which comprises:

(a) treating the pyrrolidone having the structure:

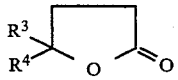

wherein $R^3$ and $R^4$ are independently the same or different and are H, or a linear or branched chain alkyl, or linear or branched alkylaryl, hydroxyalkyl, or aryl with an alkylating agent under suitable conditions to form a compound having the structure:

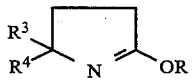

wherein $R^3$ and $R^4$ are independently the same or different and are H, or a linear or branched chain alkyl, or linear or branched alkylaryl, hydroxyalkyl, or aryl;

(b) condensing the compound formed by step (a) with Meldrum's acid in the presence of a base under conditions suitable to form a compound having the structure:

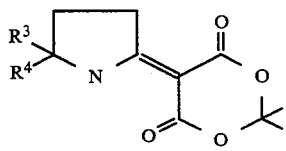

wherein $R^3$ and $R^4$ are independently the same or different and are H, or a linear or branched chain alkyl, or linear or branched alkylaryl, hydroxyalkyl, or aryl;

(c) treating the compound formed by step (b) with alkali alkoxide under conditions suitable to form a compound having the structure:

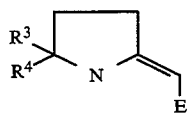

wherein $R^3$ and $R^4$ are independently the same or different and are H, or a linear or branched chain alkyl, or linear or branched alkylaryl, hydroxyalkyl, or aryl; and, E is $CO_2R$, $CONH_2$, CONHR, $CONR_2$, acyl, or CN; R is H, or a linear or branched chain alkyl, alkylaryl, or hydroxyalkyl group, (d) reacting the compound formed by step (c) with a compound having the structure:

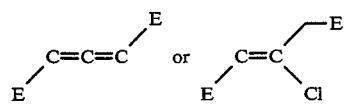

wherein E is $CO_2R$, $CONH_2$, CONHR, $CONR_2$, acyl, or CN; and, R is H, or a linear or branched chain alkyl, alkylaryl, or hydroxyalkyl group, under conditions suitable to form a compound having the structure:

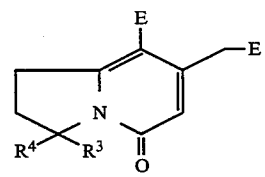

wherein $R^3$ and $R^4$ are independently the same or different and are H, or a linear or branched chain alkyl, or linear or branched alkylaryl, hydroxyalkyl, or aryl; E is $CO_2R$, $CONH_2$, CONHR, $CONR_2$, acyl, or CN; and, R is H, or a linear or branched chain alkyl, alkylaryl, or hydroxyalkyl group, (e) deprotonating the compound formed by step (d) with a non-nucleophilic base to form an anion and alkylating the anion with an electrophilic reactant under conditions suitable to form a compound having the structure:

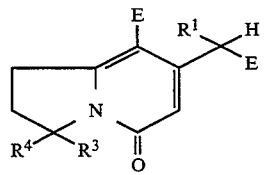

wherein E is $CO_2R$, $CONH_2$, CONHR, $CONR_2$, acyl, or CN; $R^1$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, (f) reacting the compound formed by step (e) with a carbonyl compound having the structure $R^2$—CHO, wherein $R^2$ is H, or a linear or branched chain alkyl, alkylaryl, or hydroxyalkyl group, or an aryl group, under suitable conditions to form a compound having the structure:

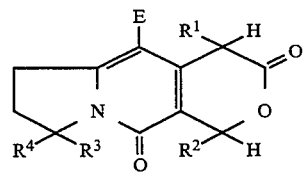

wherein E is $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group;

(g) hydrolyzing and decarboxylating the compound formed by step (f) under suitable acidic conditions to form a compound having the structure:

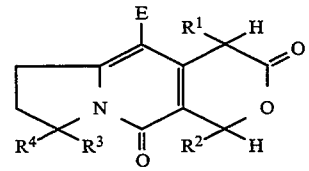

wherein E is H; $R^1$, $R^2$, $R^3$, and $R^4$ are independently the same or different and are H, or a linear or branched chain alkyl, alkylaryl, or hydroxyalkyl group, or an aryl group;

(h) treating the compound formed by step (g) with an hydroxylating reagent under conditions suitable to form the compound having the structure:

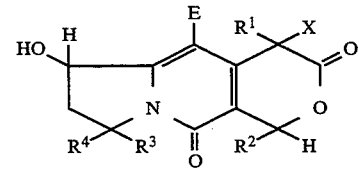

wherein E is H; X is OH; $R^1$, $R^2$, $R^3$, and $R^4$ are independently the same or different and are H, or a linear or branched chain alkyl, alkylaryl, or hydroxyalkyl group, or an aryl group.

The present invention provides a process of synthesizing a compound having the structure:

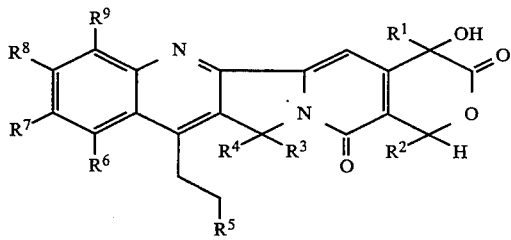

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, which comprises:

(a) treating an arylaldehyde having the structure:

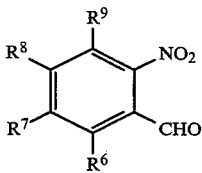

wherein $R^6$, $R^8$, and $R^9$ are independently the same or different and are H, or a linear or branched chain alkyl, alkylaryl, alkoxy, aminoalkoxy, or hydroxyalkyl group, or an aryl, aryloxy, or nitro group, or $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, with a vinylic organometallic reagent having the structure:

R5—CH=CH—M wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$, and M is Li, K, Na, MgCl, or MgBr; to form a compound having the structure:

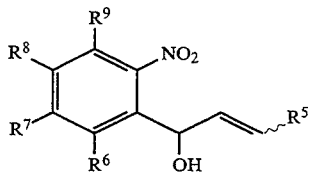

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$; and, n is an integer from 0 to 9;

(b) oxidizing the compound formed in step (a) with an oxidizing agent under suitable conditions to form a compound having the structure:

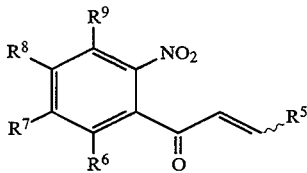

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$; $R^6$, $R^8$, and $R^9$ are independently the same or different and are H, or a linear or branched chain alkyl, alkylaryl, alkoxy, aminoalkoxy, or hydroxyalkyl group, or an aryl, aryloxy, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9;

(c) reducing the compound formed in step (b) under suitable conditions to form a compound having the structure:

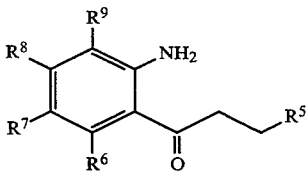

wherein $R^5$ is a linear or branched chain alkyl, alkylaryl, alkoxyalkyl, aryloxyalkyl, or hydroxy alkyl group, or an aryl group, or $(CH_2)_nNR^{11}R^{12}$, or $(CH_2)_nOR^{11}$; $R^6$, $R^8$, and $R^9$ are independently the same or different and are H, or a linear or branched chain alkyl, alkylaryl, alkoxy, aminoalkoxy, or hydroxyalkyl group, or an aryl, or aryloxy, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9;

(d) condensing the compound formed in step (c) with a compound having the structure:

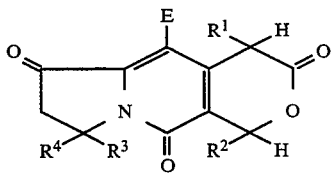

wherein E is H, COaR, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; in the presence of an acid catalyst under suitable conditions to form a compound having the structure:

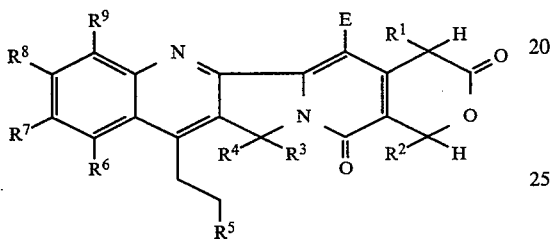

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_n NR^{11}R^{12}$, or $(CH_2)_n OR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9;

(e) hydrolyzing and decarboxylating the compound formed in step (d) using an acid under suitable conditions to form a compound having the structure:

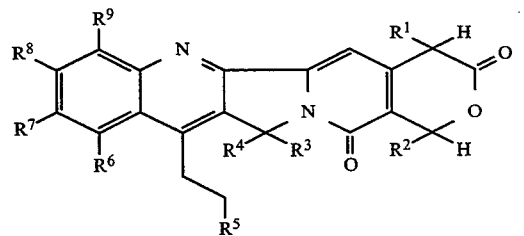

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxy alkyl group, or an aryl group, or $(CH_2)_2NR^{11}R^{12}$ or $(CH_2)_n OR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9; and, (f) treating the compound formed in step (e) with a hydroxylating reagent under suitable conditions to form a compound having the structure:

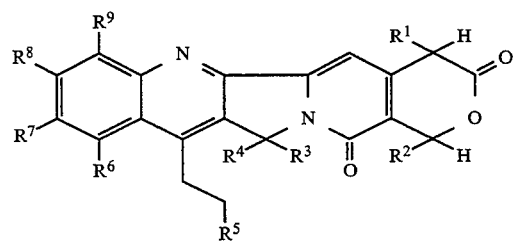

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_n NR^{11}R^{12}$, or $(CH_2)_n OR^{11}$; $R^7$ is OH, or a linear or branched chain or alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9.

The invention also provides a process of synthesizing a compound having the structure:

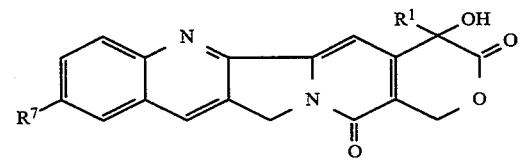

wherein $R^1$ is ethyl and $R^7$ is OH, which comprises:
(a) condensing a compound having the structure:

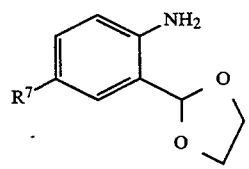

wherein $R^7$ is OH with a compound having the structure:

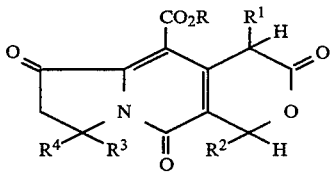

wherein R is H, or a linear or branched chain alkyl, alkylaryl, or hydroxyalkyl group, or an aryl group; $R^1$ is ethyl; $R^2$ $R^3$ and $R^4$ are H; and, $R^7$ is OR, with a suitable acidic catalyst comprising p-toluenesulfonic acid in toluene to form a compound having the structure:

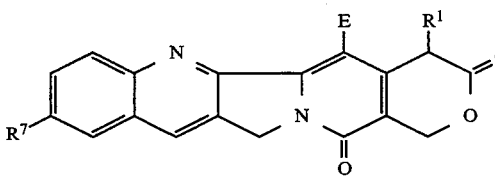

wherein R is H, or a linear or branched chain alkyl, alkylaryl, or hydroxyalkyl group, or an aryl group; $R^1$ is ethyl; and, $R^7$ is OR;

(b) hydrolyzing and decarboxylating the compound formed in step (a) with a suitable acid comprising hydrobromic acid to form a compound having the structure:

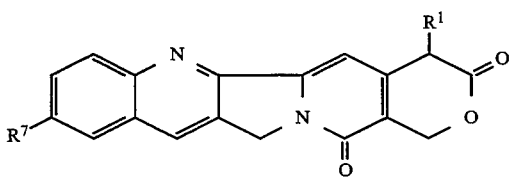

wherein $R^1$ is ethyl and $R^7$ is OR; and, (c) treating the compound formed in step (b) with a hydroxylating reagent under suitable conditions to form a compound having the structure:

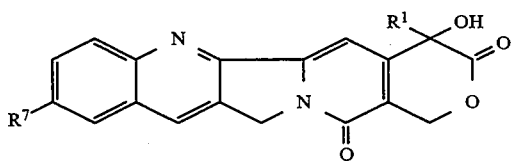

wherein $R^1$ is ethyl and $R^7$ is OH.

The invention further provides a process of synthesizing a compound having the structure:

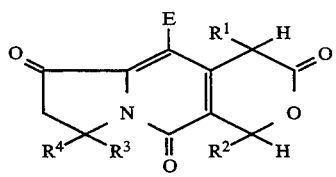

wherein E is H, $CO_2R$, $CONH_2$, CONHR, $CONR_2$, or CN; $R^1$, $R^2$, $R^3$ and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) treating a compound having the structure:

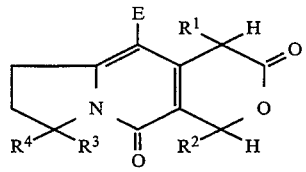

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; with a hydroxylating reagent under suitable conditions to form a compound having the structure:

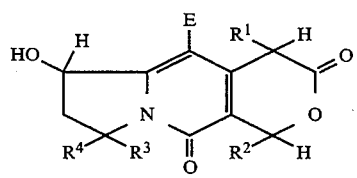

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) oxidizing the compound formed by step (a) with an oxidant under suitable conditions to form a compound having the structure:

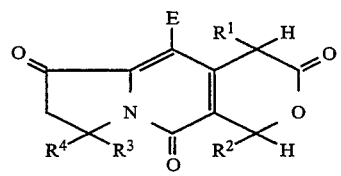

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group.

The invention additionally provides a process of synthesizing a compound having the structure:

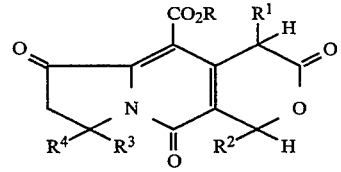

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) condensing an aryl aldehyde with a compound having the structure:

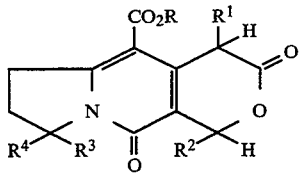

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, with a basic reagent under suitable conditions to form a compound having the structure:

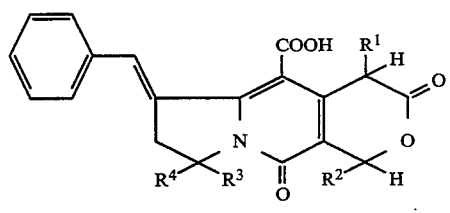

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) ozonolyzing the compound formed by step (a) under suitable conditions to form a compound having the structure:

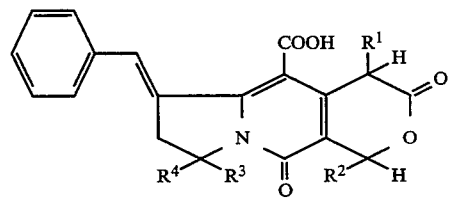

wherein $R^1$, $R^2$, $R^3$, and $R^4$ are independently the same or different and are H, or a linear or branched chain alkyl, alkylaryl, or hydroxyalkyl group, or an aryl group; and, (c) re-esterifying the compound formed in step (b) with a suitable reagent under suitable conditions to form a compound having the structure:

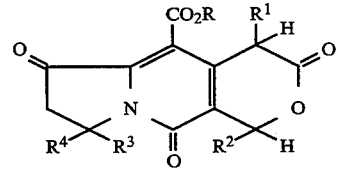

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group.

The invention also provides a process of synthesizing a compound having the structure:

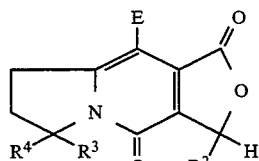

wherein E is H, $CO_2R$, $CONH_2$, CONHR, $CONR_2$, or CN; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9, which comprises:

(a) preparing a compound having the structure:

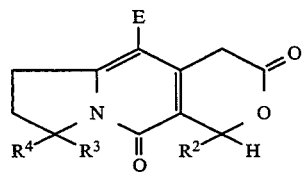

wherein E is H, $CO_2R$, $CONH_2$, CONHR, $CONR_2$, or CN; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9;

(b) treating the compound formed in step (a) with a hydroxylating reagent under suitable conditions to form a compound having the structure:

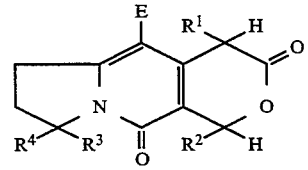

wherein E is H, $CO_2R$, $CONH_2$, CONHR, $CONR_2$, or CN; $R^1$ is OH; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9; and, (c) oxidizing the compound formed in step (b) with an oxidant under suitable conditions to form the compound having the structure:

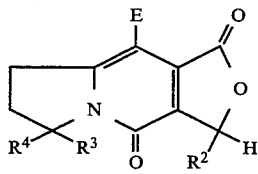

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group.

The invention further provides a process of synthesizing a compound having the structure:

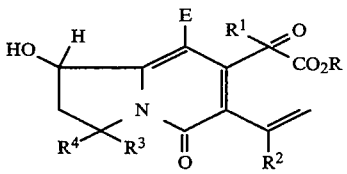

wherein E is H CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group, which comprises:

(a) preparing a compound having the structure:

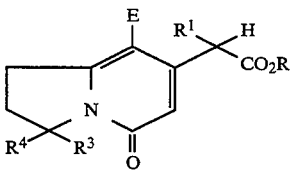

wherein E is H, CO$_2$R, CONH$_2$, CONHR, CONR$_2$, or CN; R$^1$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(b) reacting the compound formed in step (a) with a halogenating reagent to form a compound having the structure:

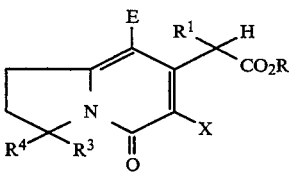

wherein X is Br, Cl, or I; E is H, CO$_2$R, CONH$_2$, CONHR, CONR$_2$, or CN; R$^1$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(c) cross-coupling the compound formed in step (b) with an organometallic reagent having the structure:

wherein M is a trialkylstannyl moiety and R$^2$ is H, or a linear or branched chain alkyl, alkylaryl, or hydroxyalkyl group, or an aryl group, under suitable conditions to form a compound having the structure:

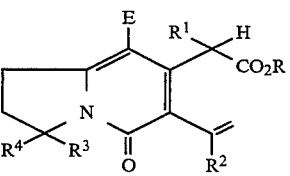

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group; and, (d) treating the compound formed in step (c) with a base and a hydroxylating reagent under suitable conditions to form a compound having the structure:

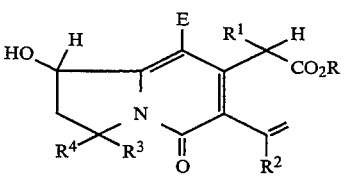

wherein E is H, CO$_2$R, CONH$_2$, CONHR, CONR2, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group.

The invention further provides a process of synthesizing a compound having the structure:

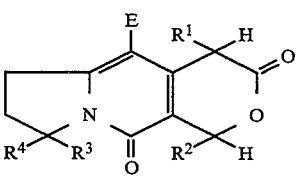

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group, which comprises:

(a) preparing a compound having the structure:

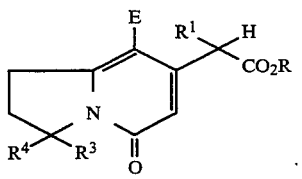

wherein E is H, CO$_2$R, CONH$_2$, CONHR, CONR$_2$, or CN; R$^1$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(b) treating the compound formed in step (a) with a basic reagent under suitable conditions to form a compound having the structure:

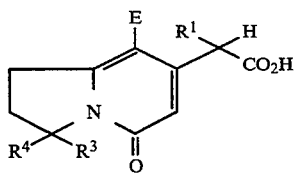

wherein E is H, CO$_2$R, CONH$_2$, CONHR, CONR$_2$, or CN; R is H, or a linear or branched chain alkyl, alkylaryl, or hydroxyalkyl group, or an aryl group; R$^1$, R$^3$, and R$^4$ are independently the same or different and are H, or a linear or branched chain alkyl, alkylaryl, or hydroxyalkyl group, or an aryl group; and, (c) condensing the compound formed in step (b) with an aldehyde R$^2$—CHO under suitable conditions to form a compound having the structure:

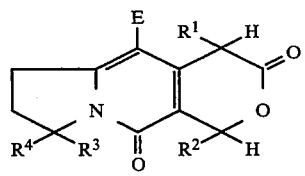

wherein E is H, CO$_2$R, CONH$_2$, CONH$_2$, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group; and, R is H, or a linear or branched chain alkyl, alkylaryl, or hydroxyalkyl group, or an aryl group.

DETAILED DESCRIPTION OF THE INVENTION

The present invention provides new analogues of camptothecin, an anti-cancer compound having the structure:

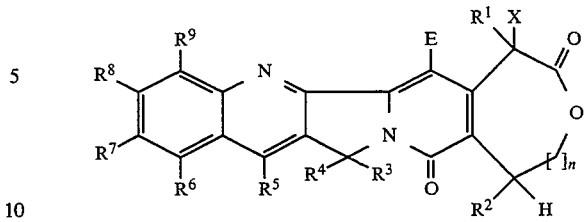

wherein E is H, CO$_2$R, CONH$_2$, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or a C-glycal, or CO$_2$R, nitro, cyano, Cl, F, Br, I, SR$^{10}$, NR$^{11}$R$^{12}$, OR$^{13}$; R is H or a linear or branched chain alkyl, alkylaryl, or hydroxyalkyl group or an aryl group; R$^{10}$, R$^{11}$ and R$^{12}$ are independently the same or different and are H, or a linear or branched chain alkyl, alkylaryl, or acyl group, or an aryl group; R$^{13}$ is glycosyl; n is 0 or 1; with the proviso that when R$^1$ is ethyl, and n is 0, E, R$^2$, R$^3$ and R$^4$ are not all H. In one embodiment of the invention, E is H; in another embodiment, E is CO$_2$R and R is preferably selected from the group consisting of methyl, ethyl, propyl, butyl, benzyl, and phenyl. In certain embodiments, R$^1$ is ethyl; while in certain other embodiments, R$^2$ is CH$_3$. In certain embodiments, X preferably OH; while in still other embodiments, X is H.

The invention also provides a tricyclic intermediate useful for preparing camptothecin analogues, which has the structure:

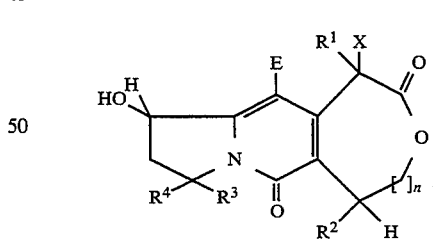

wherein E is H, CO$_2$R, CONH$_2$, CONHR, CONR$_2$, acyl, or CN; X is H, OH, or OR; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, with the proviso that when R$^1$ is ethyl, and n is 0, E, R$^2$, R$^3$, and R$^4$ are not all H.

The invention further provides another intermediate useful for synthesizing camptothecin analogues having the structure:

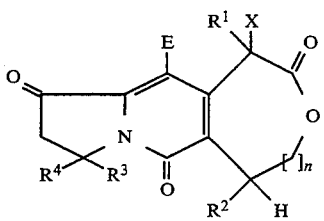

wherein E is H, $CO_2R$, $CONH_2$, CONHR, $CONR_2$, acyl, or CN; X is H, OH, or OR; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, with the proviso that when $R^1$ is ethyl, and n is 0, E, $R^2$, $R^3$, and $R^4$ are not all H.

The invention provides a process of synthesizing the intermediate compound having the structure:

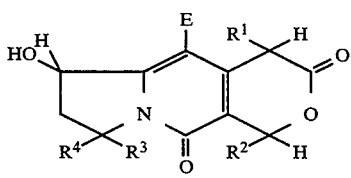

wherein E is H; X is OH; $R^1$, $R^2$, $R^3$, and $R^4$ are independently the same or different and are H, or a linear or branched chain alkyl, alkylaryl, or hydroxyalkyl group, or an aryl group; which comprises:

(a) treating the pyrrolidone having the structure:

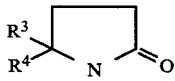

wherein $R^3$ and $R^4$ are independently the same or different and are H, or a linear or branched chain alkyl, alkylaryl, or hydroxyalkyl group, or an aryl group, with an alkylating agent under suitable conditions to form a compound having the structure:

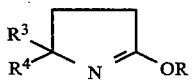

wherein $R^3$ and $R^4$ are independently the same or different and are H, or a linear or branched chain alkyl, alkylaryl, or hydroxyalkyl group, or an aryl group;

(b) condensing the compound formed by step (a) with Meldrum's acid in the presence of a base under conditions suitable to form a compound having the structure:

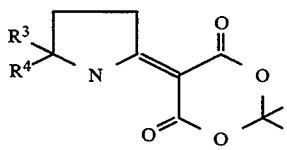

wherein $R^3$ and $R^4$ are independently the same or different and are H, or a linear or branched chain alkyl, alkylaryl, or hydroxyalkyl group, or an aryl group;

(c) treating the compound formed by step (b) with alkali alkoxide under conditions suitable to form a compound having the structure:

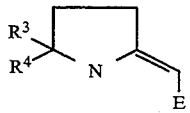

wherein $R^3$ and $R^4$ are independently the same or different and are H, or a linear or branched chain alkyl, or linear or branched alkylaryl, hydroxyalkyl, or aryl; and, E is $CO_2R$, $CONH_2$, CONHR, $CON_2$, acyl, or CN; R is H, or a linear or branched chain alkyl, alkylaryl, or hydroxyalkyl group, (d) reacting the compound formed by step (c) with a compound having the structure:

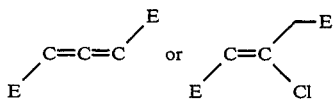

wherein E is $CO_2R$, $CONH_3$, CONHR, $CON_2$, acyl, or CN; and, R is H, or a linear or branched chain alkyl, alkylaryl, or hydroxyalkyl group, under conditions suitable to form a compound having the structure:

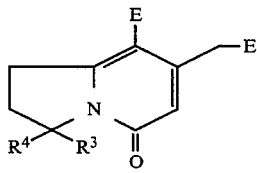

wherein $R^3$ and $R^4$ are independently the same or different and are H, or a linear or branched chain alkyl, alkylaryl, or hydroxyalkyl group, or an aryl group; E is $CO_2R$, $CONH_2$, CONHR, $CONR_2$, acyl, or CN; and, R is H, or a linear or branched chain alkyl, alkylaryl, or hydroxyalkyl group, (e) deprotonating the compound formed by step (d) with a non-nucleophilic base to form an anion and alkylating the anion with an electrophilic reactant under conditions suitable to form a compound having the structure:

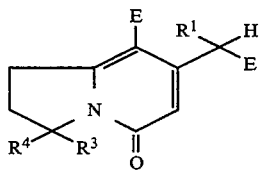

wherein E is $CO_3R$, $CONH_2$, CONHR, $CONR_2$, acyl, or CN; $R^1$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group;

(f) reacting the compound formed by step (e) with a carbonyl compound having the structure $R^2$-CHO, wherein $R^2$ is H, or a linear or branched chain alkyl, alkylaryl, or hydroxyalkyl group, or an aryl group, under suitable conditions to form a compound having the structure:

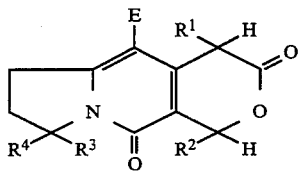

wherein E is $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group;

(g) hydrolyzing and decarboxylating the compound formed by step (f) under suitable acidic conditions to form a compound having the structure:

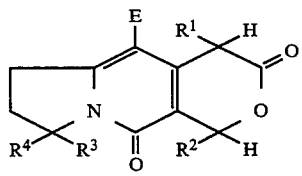

wherein E is H; $R^1$, $R^2$, $R^3$, and $R^4$ are independently the same or different and are H, or a linear or branched chain alkyl, alkylaryl, or hydroxyalkyl group, or an aryl group;

(h) treating the compound formed by step (g) with an hydroxylating reagent under conditions suitable to form the compound having the structure:

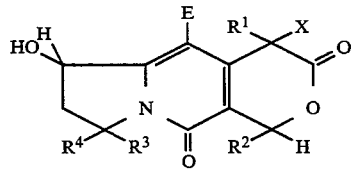

wherein E is H; X is OH; $R^1$, $R^2$, $R^3$, and $R^4$ are independently the same or different and are H, or a linear or branched chain alkyl, alkylaryl, or hydroxyalkyl group, or aryl.

The process of step (a) above may be effected using a variety of alkylating reagents, known to those skilled in the art, but is preferably dimethyl sulfate. The process of step (b) results on heating the lactim ether with an active methylene condensing agent, preferably Meldrum's acid, in the presence of a tertiary amine base in an inert solvent such as benzene, at a temperature sufficient to cause reaction, preferably at the reflux temperature. The condensation product is then converted in process step (c) to the unsaturated decarboxylated product by heating the product of step (b) with an alkali metal alkoxide or aryloxide in its corresponding alcohol as solvent or cosolvent at a temperature sufficient to cause reaction, preferably at the reflux temperature of the solvent. Process step (d) may be effected by treating the decarboxylated product with a disubstituted allene in the presence of a tertiary organic base, preferably triethylamine, in an alcoholic solvent, preferably absolute ethanol, at a temperature sufficient to cause reaction, preferably at room temperature. The reaction takes from 40 to 80 hours, and most usually about 65 hours. The resulting pyridone is deprotonated in step (e) using a non-nucleophilic base, preferably potassium t-butoxide, in an anhydrous dipolar solvent, such as dimethoxyethane, at a temperature adequate to cause reaction, but low enough to prevent side-reactions, preferably at $-78°$ C. The resulting deprotonated species is then alkylated or arylated with an electrophilic reagent, most commonly an alkyl halide, tosylate, or aryne intermediate, but preferably a primary or secondary alkyl bromide or iodide, and may be driven to completion by warming the reaction mixture to room temperature and stirring for a time depending on the specific alkylating agent, but usually between 2 and 50 hours. Step (f) entails heating the alkylated heterocyclic compound with an alkyl or aryl aldehyde in the presence of an acid catalyst, preferably an organic sulfonic acid or a mineral acid, more preferably concentrated sulfuric acid, in a solvent inert to the reaction conditions, preferably aqueous dioxane. The reaction is preferably carried out in a thick wall tube or other high-pressure reaction vessel, at a temperature sufficient to cause reaction, generally between 90° C. and 160° C., and preferably at 107° C., for about 24 hours. The process of step (g) may be effected by heating a mixture of the lactone formed in step (f) in a mineral acid, preferably concentrated aqueous hydrobromic acid, at a temperature sufficient to produce the desired product, generally between preferably between 90° C. and 140° C., and more preferably at 105° C., for about 18 hours. The process of hydroxylating step (h) is accomplished by heating a mixture of the product of step (g) in a solvent inert to the reaction conditions, such as aqueous dioxane, with an hydroxylating reagent, preferably selenium dioxide, at a temperature sufficient to cause reaction, but not to degrade the starting material, preferably between 120° C. and 180° C., more preferably at 155° C.

The invention also provides a process of synthesizing the intermediate compound having the structure:

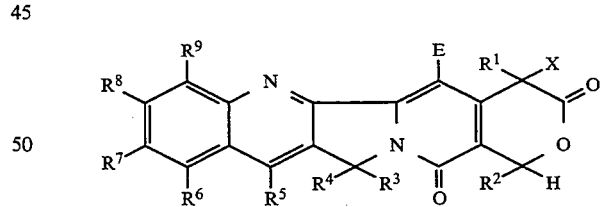

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

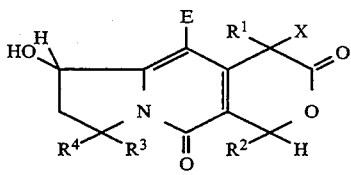

wherein E is H; X is OH; and, $R^1$, $R^2$, $R^3$, and $R^4$ are independently the same or different and are H, or a linear or branched chain alkyl, alkylaryl, or hydroxyalkyl group, or an aryl group, as described above;

(b) oxidizing the compound formed in step (a) with an oxidant under suitable conditions to form a compound having the structure:

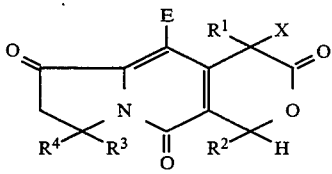

wherein E is H; X is OH; $R^1$, $R^2$, $R^3$, and $R^4$ are independently the same or different and are H, or a linear or branched chain alkyl, alkylaryl, or hydroxyalkyl group, or an aryl group;

(c) condensing the compound formed by step (b) with a compound having structure:

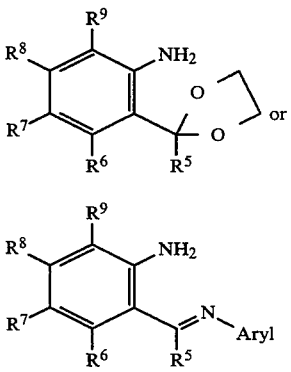

wherein $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, under suitable conditions to form the compound having the structure:

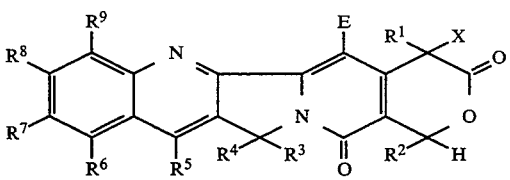

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group.

The invention provides a process of synthesizing substituted analogues of camptothecin, a compound having the structure:

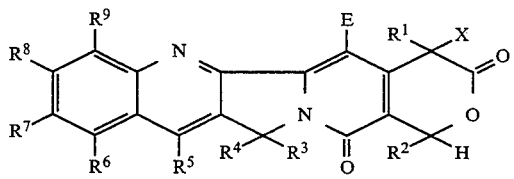

wherein E is H; X is OH; $R^1$, $R^2$, $R^3$, and $R^4$ are independently the same or different and are H, or a linear or branched chain alkyl, alkylaryl, or hydroxyalkyl group or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro $CO_2R$, cyano, Cl, F, Br, I, $SR^{10}$, or $NR^{11}R^{12}$; R is H, or a linear or branched chain alkyl, alkylaryl, or hydroxyalkyl group or an aryl group; $R^{10}$, $R^{11}$ and $R^{12}$ are independently the same or different and are H, a linear or branched chain alkyl, alkylaryl, or acyl group, or an aryl group, which comprises:

(a) preparing a compound having the structure:

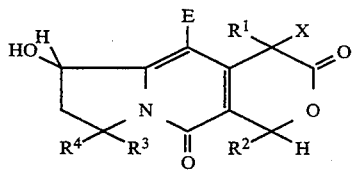

wherein E is H; X is OH; and, $R^1$, $R^2$, $R^3$, and $R^4$ are independently the same or different and are H, or a linear or branched chain alkyl, alkylaryl, or hydroxyalkyl group, or an aryl group, as described above;

(b) oxidizing the compound formed in step (a) with an oxidant under suitable conditions to form a compound having the structure:

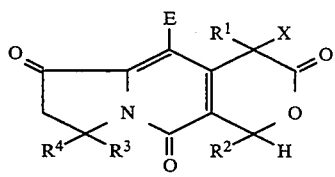

wherein E is H; X is OH; $R^1$, $R^2$, $R^3$, and $R^4$ are independently the same or different and are H, or a linear or branched chain alkyl, alkylaryl, or hydroxyalkyl group, or an aryl group;

(c) condensing the compound formed by step (b) with a compound having structure:

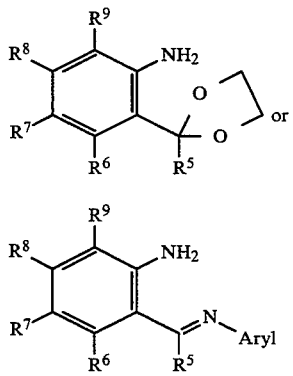

wherein $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, a linear or branched chain alkyl, alkylaryl, or acyl group, or an aryl group, under suitable conditions to form the compound having the structure:

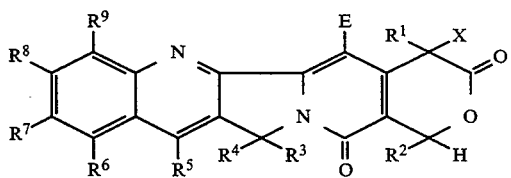

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxygroup, or an aryl or aryloxy group, or nitro, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group.

The process of step (b) is best performed using the oxidant pyridinium dichromate in the presence of activated powdered 4 Å molecular sieves in an inert solvent such as methylene dichloride at a temperature sufficient to result in the desired reaction, usually between −20° C. and 40° C., but preferably about 0° C. The condensation of step (c) is carried out by mixing the tricyclic ketone generated by step (a) with a protected ortho-amino aldehyde or ketone in an inert solvent, such as benzene or toluene, and heating to the reflux temperature of the solvent in the presence of an acid or basic catalyst. Acidic catalysts include mineral acids, such as sulfuric acid, nitric acid, phosphoric acid, and hydrochloric acid, organic alkanoic and sulfonic acids, such as acetic acid or propionic acid. The preferred catalyst is a mild acid, such as toluenesulfonic acid. A large variety of ortho-amino aldehydes and ketones are available from commercial sources, allowing the prepration of many substitution patterns, while other ortho-amino aldehydes and ketones can be prepared by methods well-known in the art. The reaction is carried out in a solvent inert to the reaction. Aromatic solvents are particularly well suited to the purpose, including benzene and toluene. When the solvent is not miscible with water, the reaction is best effected by azeotropic trapping of water generated in the process.

The invention also provides a process of synthesizing intermediates useful for preparing camptothecin analogues having the structure:

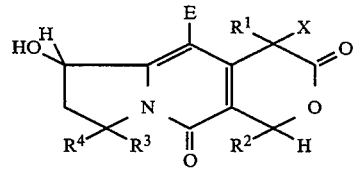

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, which comprises:

(a) preparing a compound having the structure:

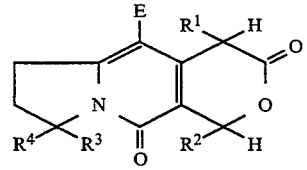

wherein E is $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, as described above; and, (b) treating the compound formed in step (a) with an hydroxylating reagent under suitable conditions to form the compound having the structure:

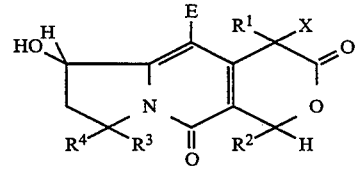

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group.

The process of the preparing step (a) is carried out as described above. The process of the treating step (b) may be accomplished by heating a mixture of the product of preparing step (a) in a solvent inert to the reaction conditions, such as aqueous dioxane, with an hydroxylating reagent, preferably selenium dioxide, at a temperature sufficient to cause reaction, but not to degrade the starting material, preferably between 120° C. and 180° C., more preferably at 155° C.

The invention also provides a process of synthesizing tricyclic intermediates useful for preparing camptothecin analogues. The intermediates have the structure:

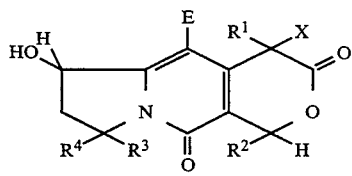

wherein E is CO$_2$R, CONH$_2$, CONHR, CONR$_2$, acyl, or CN; X is OH; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, which comprises:

(a) preparing a compound having the structure:

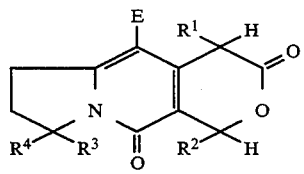

wherein E is CO$_2$R, CONH$_2$, CONHR, CONR$_2$, acyl, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, as described above; and, (b) treating the compound formed in step (a) with an hydroxylating reagent under suitable conditions to form the compound having the structure:

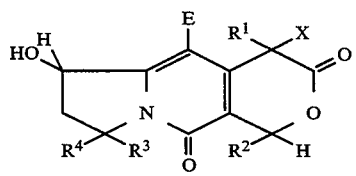

wherein E is CO$_2$R, CONH$_2$, CONHR, CONR$_2$, acyl, or CN; X is OH; R$^1$, R$^2$, R$^3$, and R$^4$ are independently the same or different and are H, or a linear or branched chain alkyl, alkylaryl, or hydroxyalkyl group, or an aryl group; and, R is H, a linear or branched chain alkyl, alkylaryl, or hydroxyalkyl group, or an aryl group.

The invention provides another variant process of synthesizing camptothecin analgues having the structure:

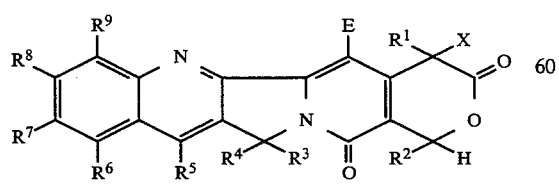

wherein E is CO$_2$R, CONH$_2$, CONHR, CONR$_2$, acyl, or CN; X is OH; R$^1$, R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy, or nitro, CO$_2$R, cyano, Cl, F, Br, I, SR$^{10}$, or NR$^{11}$R$^{12}$; R is H or a linear or branched chain alkyl, alkylaryl, or hydroxyalkyl group, or an aryl group; R$^{10}$, R$^{11}$ and R$^{12}$ are independently the same or different and are H, a linear or branched chain alkyl, alkylaryl, or acyl group, or an aryl group, which comprises:

(a) preparing a compound having the structure:

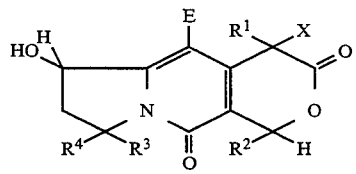

wherein E is CO$_2$R, CONH$_2$, CONHR, CONR$_2$, acyl, or CN; X is OH; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above;

(b) oxidizing the compound formed in step (a) with an oxidant under suitable conditions to provide a compound having the structure:

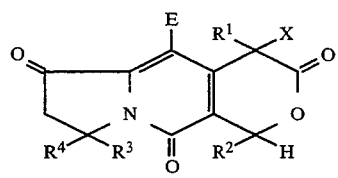

wherein E is CO$_2$R, CONH$_2$, CONHR, CONR$_2$, acyl, or CN; X is OH; R$^1$m R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, and, (c) condensing the compound formed by step (d) with a compound having structure:

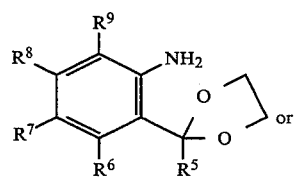

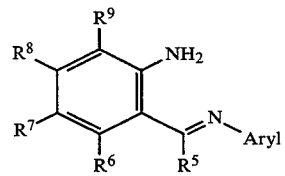

wherein R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, under suitable conditions to form the compound having the structure:

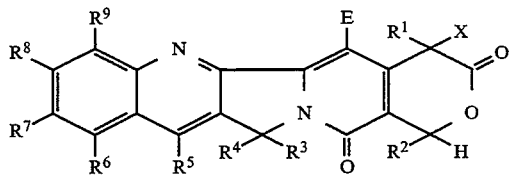

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group; and $R^{10}$, $R^{11}$ and $R^{12}$ are independently the same or different and are H, a linear or branched chain alkyl, alkylaryl, or acyl group, or an aryl group.

The process of the oxidizing step (b) is best effected using pyridinium dichromate in the presence of powdered 4 Å molecular sieves in an inert solvent such as methylene dichloride at 0°–5° C.

The invention further provides a process of synthesizing a compound having the structure:

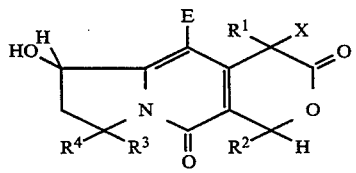

wherein E is H, $CO_2R$, $CONH_2$, CONHR, $CONR_2$, acyl, or CN; X is H or OH; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, which comprises:

(a) preparing a compound having the structure:

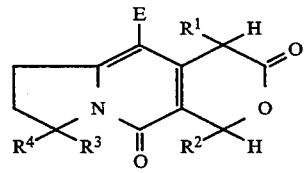

wherein E is H, $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above; and, (b) treating the compound formed in step (a) with an hydroxylating agent comprising potassium hexamethyldisilamide and a reagent having the structure:

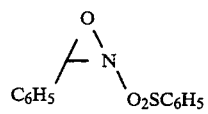

under suitable conditions to form the compound having the structure:

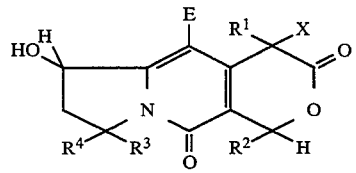

wherein E is H, $CO_2R$, $CONH_2$, CONHR, $CONR_2$, acyl, or CN; X is H or OH; $R^1$, $R^2$, $R^3$, and $R^4$ are independently the same or different and are H, or a linear or branched chain alkyl, alkylaryl, or hydroxyalkyl group, or an aryl group; R is H, a linear or branched chain alkyl, alkylaryl, or hydroxyalkyl group, or an aryl group.

The invention also provides a process of synthesizing a compound having the structure:

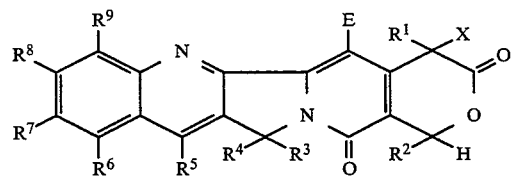

wherein E is H, $CO_2R$, $CONH_2$, CONHR, $CONR_2$, acyl, or CN; X is H; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy, group, or nitro, $CO_2R$, cyano, Cl, F, Br, I, $SR^{10}$, $NR^{11}R^{12}$; R is H, or a linear or branched chain alkyl, alkylaryl, or hydroxyalkyl group, or an aryl group; $R^{10}$, $R^{11}$, and $R^{12}$ are independently the same or different and are H, a linear or branched chain alkyl, alkylaryl, or acyl group, or an aryl group, which comprises:

(a) preparing a compound having the structure:

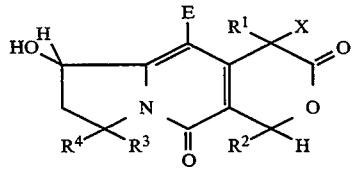

wherein E is H, $CO_2R$, $CONH_2$, CONHR, $CONR_2$, acyl, or CN; X is H; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above;

(b) oxidizing the compound formed in step (a) under suitable conditions with an oxidant to provide a compound having the structure:

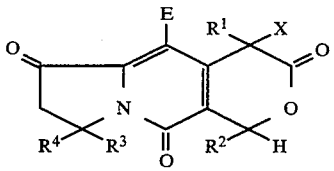

wherein E is H, CO$_2$R, CONH$_2$, CONHR, CONR$_2$, acyl, or CN; X is H; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group; and, (c) condensing the compound formed by step (b) with a compound having structure:

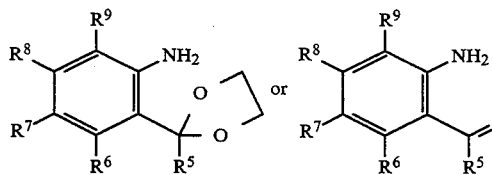

wherein R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^1$, or NR$^{11}$R$^{12}$; R is H, or a linear or branched chain alkyl, alkylaryl, or hydroxyalkyl group, or an aryl group; R$^{10}$, R$^{11}$, and R$^{12}$ are independently the same or different and are H, a linear or branched chain alkyl, alkylaryl, or acyl group, or an aryl group, under suitable conditions to form the compound having the structure:

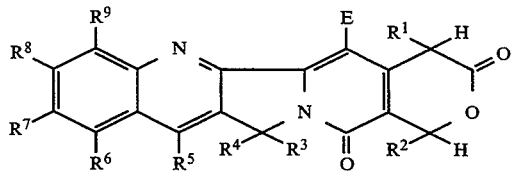

wherein E is H, CO$_2$R, CONH$_2$, CONHR, CONR$_2$, acyl, or CN; R$^1$, R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, NR$^{11}$R$^{12}$; R is H, or a linear or branched chain alkyl, alkylaryl, or hydroxyalkyl group, and, R$^{10}$, R$^{11}$ and R$^{12}$ are independently the same or different and are H, a linear or branched chain aryl, alkylaryl, or acyl group, or an aryl group.

The invention provides a process of synthesizing a compound having the structure:

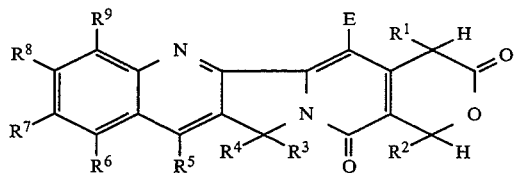

wherein E is H; R$^1$, R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; is H, or a linear or branched chain alkyl, alkylaryl, or hydroxyalkyl group, or an aryl group; R$^{10}$, R$^{11}$ and R$^{12}$ are independently the same or different and are H, a linear or branched chain alkyl, alkylaryl, or acyl group, or an aryl group, which comprises:

(a) preparing a compound having the structure:

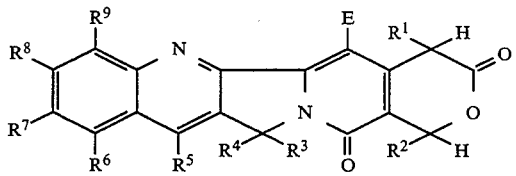

wherein E is H, CO$_2$R, CONH$_2$, CONHR, CONR$_2$, acyl, or CN; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above;

(b) hydrolyzing and decarboxylating the compound formed in step (a) under suitable conditions with an acid to provide a compound having the structure:

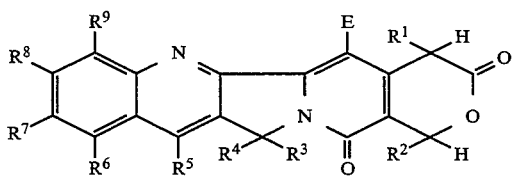

where E is H, R$^1$, R$^2$, R$^3$, and R$^4$ are independently the same or different and are H, or a linear or branched chain alkyl, alkylaryl, or hydroxyalkyl group, or an aryl group; R$^5$$^1$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, linear or branched chain alkyl, alkylaryl, or acyl group, or an aryl group.

The process of the hydrolyzing and decarboxylating step (b) is accomplished by mixing the product of the preparing step (a) with an acid, preferably an aqueous mineral acid, especially hydrobromic acid, in a sealed tube or high-pressure reaction vessel, and heating at a temperature between 100° C. and 180° C., preferably at 140° C., for 10 to 24 hours, preferably for 15 hours.

The invention also provides a process of synthesizing a compound having the structure:

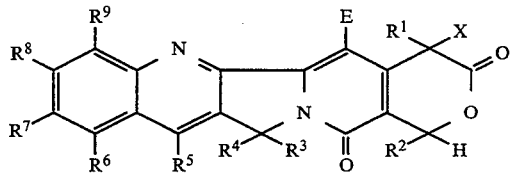

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or linear or branched chain alkyl, alkylaryl, or acyl group, or an aryl group, which comprises:

(a) preparing a compound having the structure:

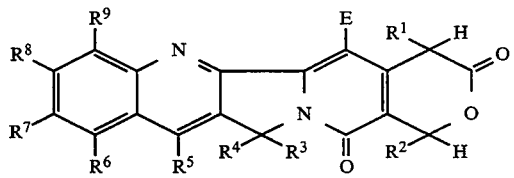

wherein E is H; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, as described above;

(b) treating the compound formed in step (a) with a hydroxylating reagent under suitable conditions to form a compound having the structure:

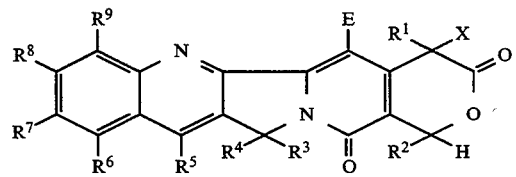

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group.

The treating step (b) is effected by dissolving the product of the preparing step (a) in a dipolar solvent, preferably dimethyformamide, and then adding a hydroxylating reagent containing a divalent ionic metal halide, preferably cupric chloride, and a base, preferably an organic base, such as dimethylamine, and then bubbling in oxygen gas over a period of time sufficient to cause completion of the process, typically about seven hours.

The invention further encompasses a process of synthesizing a compound having the structure:

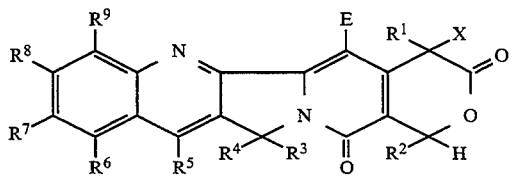

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

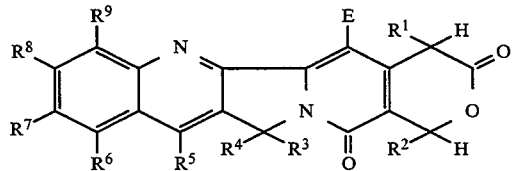

wherein E is $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$, R is H or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, as described above;

(b) treating the compound formed in step (a) with a hydroxylating reagent under suitable conditions to form a compound having the structure:

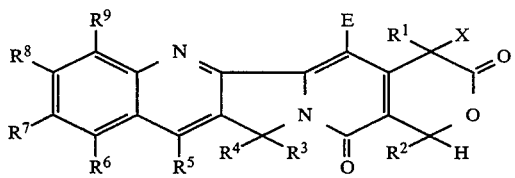

wherein E is CO₂R, CONH₂, CONHR, CONR₂, acyl, or CN; X is $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, CO₂R, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group. The hydroxylating reagent of the treating step (b) preferably comprises oxygen, cupric halide, and a base.

The invention also includes a process of synthesizing a compound having the structure:

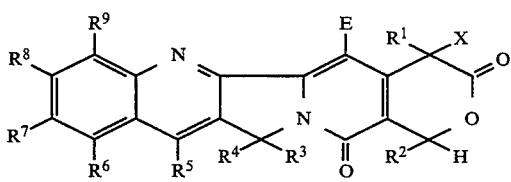

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, CO₂R, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

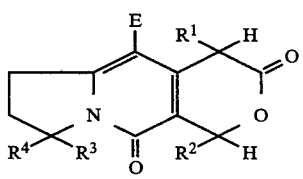

wherein E is H; $R^1$, $R^2$, $R^3$, and $R^4$ are independently the same or different and are H, or a linear or branched chain alkyl, alkylaryl, or hydroxyalkyl group, or an aryl group, as described above;

(b) treating the compound formed in step (a) with a hydroxylating reagent under conditions suitable to form the compound having the structure:

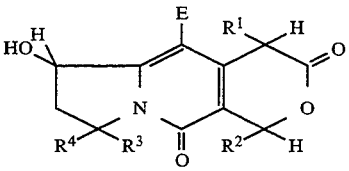

wherein E is H; $R^1$, $R^2$, $R^3$, and $R^4$ are independently the same or different and are H, or a linear or branched chain alkyl, alkylaryl, or hydroxyalkyl group, or an aryl group;

(c) oxidizing the compound formed in step (b) with an oxidant under suitable conditions to form the compound having structure:

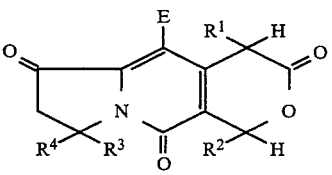

wherein E is H; $R^1$, $R^2$, $R^3$, and $R^4$ are independently the same or different and are H, or a linear or branched chain alkyl, alkylaryl, or hydroxyalkyl group, or an aryl group;

(d) condensing the compound formed in step (c) with a compound having structure:

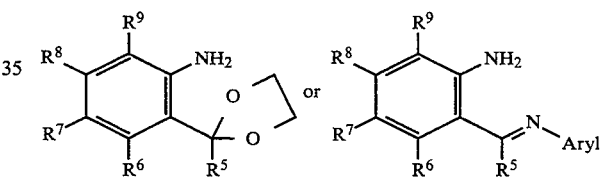

wherein $R^5$, $R^6$, $R^7$, and $R^9$ are independently the same or different and are H, or a linear or branched chain alkyl, alkylaryl, alkoxy, hydroxyalkyl, or aminoalkoxy group, or an aryl or aryloxy group, or nitro, CO₂R, cyano, Cl, F, Br, I, $SR^{10}NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, under suitable conditions to form a compound having the structure:

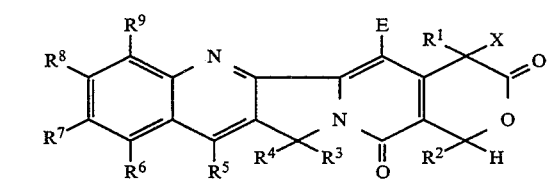

wherein E is H; X is H; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, CO₂R, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, under suitable conditions to form the compound having the structure:

(e) treating the compound formed in step (d) with a hydroxylating reagent under suitable conditions to form the compound having the structure:

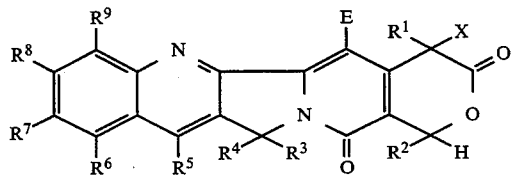

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$ and $R^9$ are independently the same or different and are H, or a linear or branched chain alkyl, alkylaryl, alkoxy, hydroxyalkyl, or aminoalkoxy group, or an aryl or aryloxy group or nitro $CO_2R$ cyano group, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group. In one embodiment of the invention, the hydroxylating reagent of the treating step (b) comprises potassium hexamethyldisilamide and a reagent having the structure:

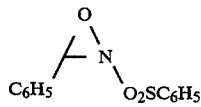

The invention also includes a process of synthesizing a compound having the structure:

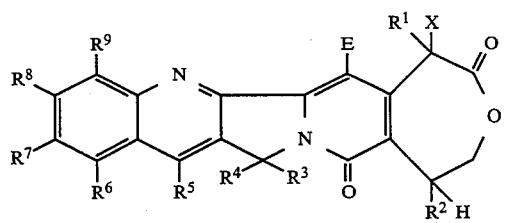

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

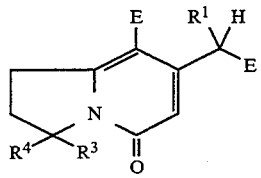

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above;

(b) halogenating the compound formed in step (a) with a halogenating agent, selected from the group comprising bromine, chlorine, and iodine under suitable conditions to form a compound having the structure:

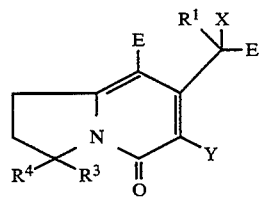

wherein E is $CO_2R$, $CONH_2$, CONHR, $CONR_2$, acyl, or CN; X is H; Y is Br, Cl, or I; $R^1$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group;

(c) treating the compound formed in step (b) with alkyl- or arylallyltrialkylstannane and a catalyst comprising palladium(0) under suitable conditions to form a compound having the structure:

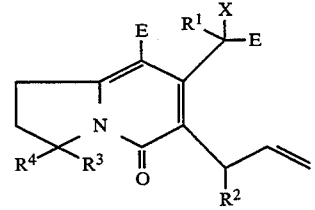

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group or an aryl group; R is H, or a linear or branched chain alkyl, alkylaryl, or hydroxyalkyl group;

(d) reacting the compound formed in step (c) with alkali metal periodate or ozone and a reducing agent comprising alkali metal borohydride, wherein the alkali metal is either lithium, sodium, or potassium, under suitable conditions to form a compound having the structure:

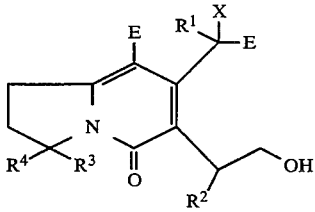

wherein E is CO$_2$R, CONH$_2$, CONHR, CONR$_2$, acyl, or CN; X is H; R$^1$, R$^3$, and R$^4$ are independently the same or different and are H, or a linear or branched chain alkyl, alkylaryl, or hydroxyalkyl group, or an aryl group; R$^2$ is a linear or branched chain alkyl group, or an aryl group; R is H, or a linear or branched chain alkyl, alkylaryl, or hydroxyalkyl group;

(e) lactonizing the compound formed in step (d) with a condensing reagent, comprising potassium trimethylsilyloxide followed by a dehydrating agent comprising N,N-dicyclohexylcarbodiimide and N,N-dimethylaminopyridine, under suitable conditions to form a compound having the structure:

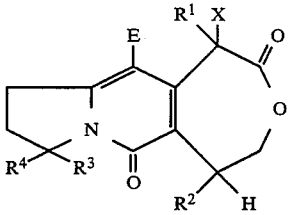

wherein E is CO$_2$R, CONH$_2$, CONHR, CONR$_2$, acyl, or CN; X is H; R$^1$, R$^3$, and R$^4$ are independently the same or different and are H, or a linear or branched chain alkyl, alkylaryl, or hydroxyalkyl group, or an aryl group; R$^2$ is a linear or branched chain alkyl group, or an aryl group; R is H, or a linear or branched chain alkyl, alkylaryl, or hydroxyalkyl group;

(f) hydroxylating the compound formed in step (e) with an hydroxylating reagent comprising the oxaziridine having the structure:

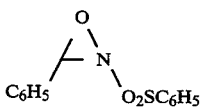

under suitable conditions to form a compound having the structure:

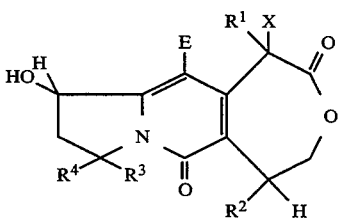

wherein E is CO$_2$R, CONH$_2$, CONHR, CONR$_2$, acyl, or CN; X is H; R$^1$, R$^3$, and R$^4$ are independently the same or different and are H, or a linear or branched chain alkyl, alkylaryl, or hydroxyalkyl group, or an aryl group; R$^2$ is a linear or branched chain alkyl group, or an aryl group; R is H, or a linear or branched chain alkyl, alkylaryl, or hydroxyalkyl group;

(g) oxidizing the compound formed in step (f) with an oxidant under suitable conditions to form a compound having the structure:

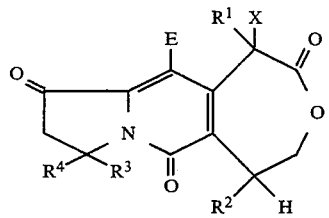

wherein E is CO$_2$R, CONH$_2$, CONHR, CONR$_2$, acyl, or CN; X is H; R$^1$, R$^3$, and R$^4$ are independently the same or different and are H, or a linear or branched chain alkyl, alkylaryl, or hydroxyalkyl group, or an aryl group; R$^2$ is a linear or branched chain alkyl group, or an aryl group; R is H, or a linear or branched chain alkyl, alkylaryl, or hydroxyalkyl group;

(h) condensing the compound formed in step (g) under suitable conditions to form a compound having the structure:

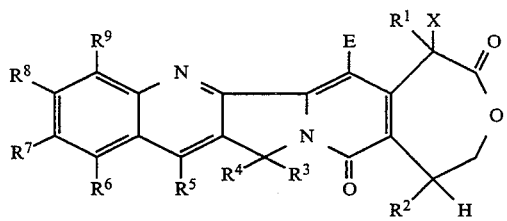

wherein E is CO$_2$R, CONH2, CONHR, CONR$_2$, acyl, or CN; X is H; R$^1$, R$^3$, and R$^4$ are independently the same or different and are H, or a linear or branched chain alkyl, alkylaryl, or hydroxyalkyl group, or an aryl group; R$^2$ is a linear or branched chain alkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$, and R$^{12}$ are independently the same or different and are H, or a linear or branched chain alkyl, alkylaryl, or acyl group, or an aryl group;

(i) hydroxylating the compound formed in step (h) with a hydroxylating reagent under suitable conditions to form a compound having the structure:

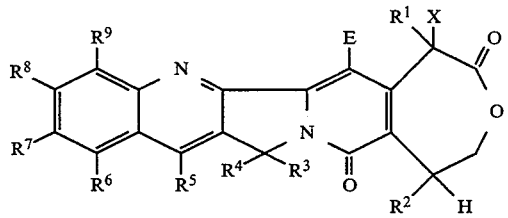

wherein E is CO$_2$R, CONH$_2$, CONHR, CONR$_2$, acyl, or CN; X is OH; R$^1$, R$^3$, and R$^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group. The oxidant of the oxidizing step (g) is favorably pyridinium dichromate. The hydroxylating reagent of step (j) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention further provides a process of synthesizing a compound having the structure:

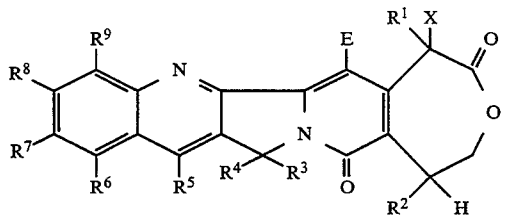

wherein E is H; X is OH; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, , or $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

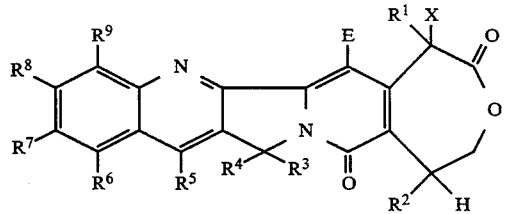

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, $NR^{11}R^{12}$; R is H or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, as described above;

(b) hydrolyzing and decarboxylating the compound formed in step (a) with an acid comprising aqueous hydrobromic acid under suitable conditions to form a compound having the structure:

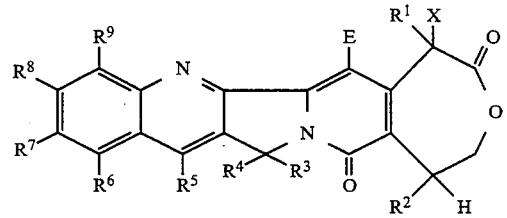

wherein E is H; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; and, (c) hydroxylating the compound formed in step (b) with a hydroxylating reagent under suitable conditions to form a compound having the structure:

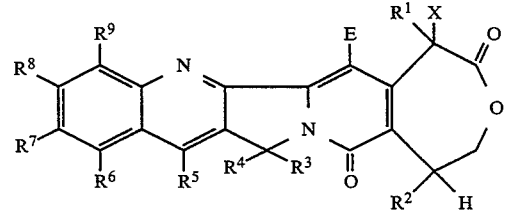

wherein E is H; X is OH; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group. The hydroxylating reagent of step (c) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention provides a process of synthesizing a compound having the structure:

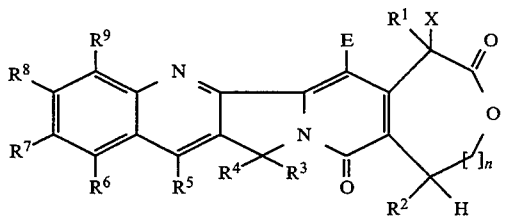

wherein E is H, CO$_2$R, CONH$_2$, CONHR, CONR$_2$, acyl, or CN; X, R$^1$ is O; R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; n is 0 or 1, which comprises:

(a) preparing a compound having the structure:

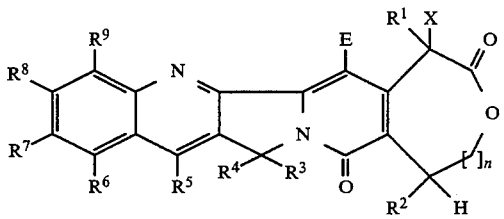

wherein R$^1$ is H; E is H, CO$_2$R, CONH$_2$, CONHR, CONR$_2$, acyl, or CN; X is H; R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; and, n is 0 or 1, as described above;

(b) hydroxylating the compound formed in step (a) with a hydroxylating reagent under suitable conditions to form a compound having the structure:

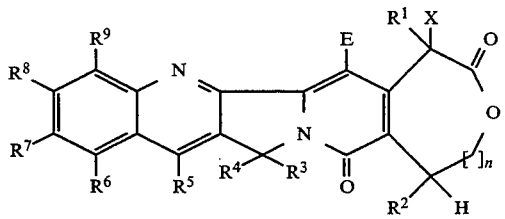

wherein E is H, CO$_2$R, CONH$_2$, CONHR, CONR$_2$, acyl, or CN; X is OH; R$^1$ is H; R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; and, n is 0 or 1; and, (c) oxidizing the compound formed in step (b) with an oxidant under suitable conditions to form a compound having the structure:

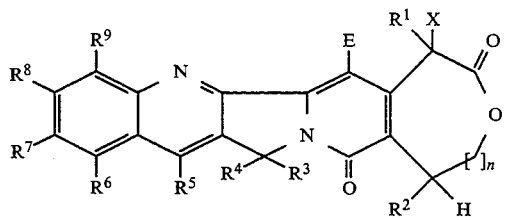

wherein E is H, CO$_2$R, CONH$_2$, CONHR, CONR$_2$, acyl, or CN; X, R$^1$ is O; R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; and, n is 0 or 1. The hydroxylating reagent of step (b) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention also encompasses a process of synthesizing enantiomerically pure compounds related to camptothecin and analogues thereof, wherein the configuration is exclusively R or S. The process comprises performing the hydroxylating step with the hydroxylating reagent having the structure:

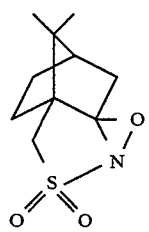

or the hydroxylating reagent of opposite configuration, 0 respectively. While the value of the racemic mixture of camptothecins provided by non-enantiospecific routes is considerable, given the high native biological activity of camptothecin, the possibility of obtaining still higher activities in an optically pure analogue suggest the clinical importance of the present invention.

The invention also includes a process of synthesizing a compound having the structure:

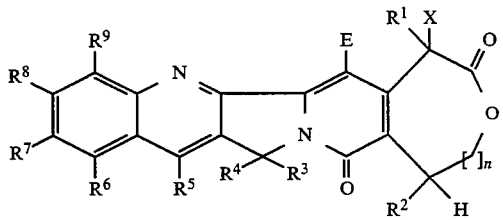

wherein E is H, CO$_2$R, CONH$_2$, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; one or more of the group R$^5$, R$^6$, R$^7$, R$^8$, and R$^9$ are C-glycal, and the others are independently the same or different and are H, or a linear or branched chain alkyl, alkylaryl, alkoxy, hydroxyalkyl, or aminoalkoxy group, or an aryl or aryloxy group, or nitro, CO$_2$aR, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; and, n is 0 or 1, which comprises:

(a) preparing a compound having the structure:

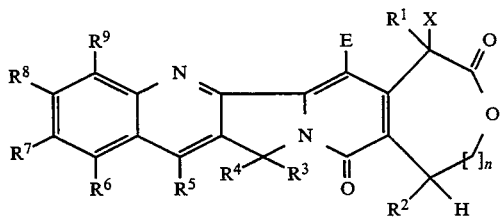

wherein g is H, CO$_2$R, CONH$_2$, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalky group, or an aryl group; one or more of the group R$^5$, R$^6$, R$^7$, R$^8$, and R$^9$ are OR$^{13}$, and the others are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; R$^{13}$ is H; and, n is 0 or 1, as described above;

(b) reacting the compound formed in step (a) with a reagent comprising PhN(CF$_3$SO$_2$)$_2$ under suitable conditions to form a triflate compound having the structure:

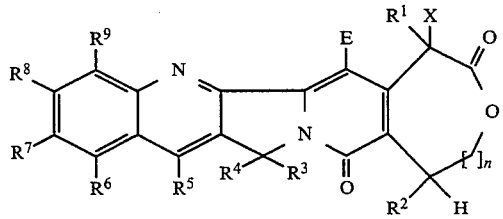

wherein E is H, COrR, CONHr, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; one or more of the group R$^5$, R$^6$, R$^7$, R$^8$, and R$^9$ are OR$^{13}$, and the others are independently the same or different and are H, or a linear or branched chain alkyl, alkylaryl, alkoxy, hydroxyalkyl, or aminoalkoxy group, or an aryl or aryloxy group, or nitro, cyano, CO$_2$R, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; R$^{13}$ is SO$_2$CF$_3$; and, n is 0 or 1; and, (c) coupling the compound formed in reacting step (b) with a stannylated glycal under suitable conditions to form the compound having the structure:

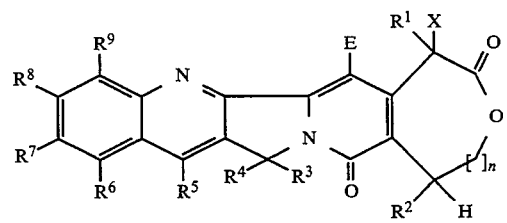

wherein E is H, COrR, CONH$_2$, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; one or more of the group R$^5$, R$^6$, R$^7$, R$^8$, and R$^9$ are OR$^{13}$, and the others are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; R$^{13}$ is c-glycal; and, n is 0 or 1.

The invention also provides a process of synthesizing a compound having the structure:

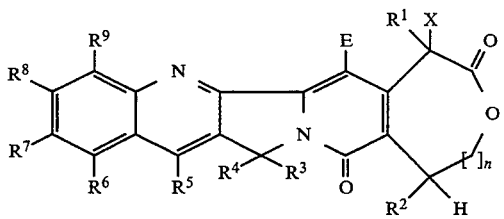

wherein E is H, CO$_2$R, CONHr, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; one or more of the group R$^5$, R$^6$, R$^7$, R$^8$, and R$^9$ are OR$^{13}$, and the others are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; R13 is a O-glycosyl; and, n is 0 or 1; which comprises:

(a) preparing a compound having the structure:

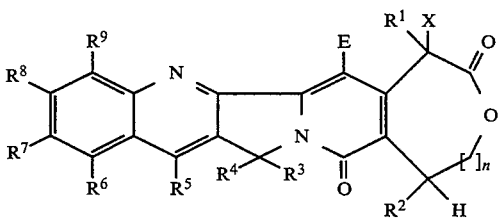

wherein E is H, CO$_2$R, CONH$_2$, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; one or more of the group R$^5$, R$^6$, R$^7$, R$^8$, and R$^9$ are OR$^{13}$, and the others are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; R$^{13}$ is H; and, n is 0 or 1; as described above; and, (b) reacting the compound formed in step (a) with a reagent comprising a glycosyl epoxide under suitable conditions to form a compound having the structure:

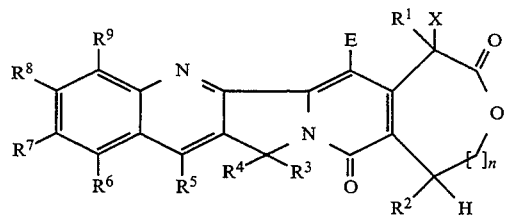

wherein E is H, CO$_2$R, CONH$_2$, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; one or more of the group R$^5$, R$^6$, R$^7$, R$^7$, and R$^9$ are OR$^{13}$, and the others are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; R$^{13}$ is O-glycosyl; and, n is 0 or 1.

The present invention provides synthetic processes for the preparation of camptothecin, an anti-cancer substance and analogues thereof. In one embodiment, the invention provides a process of synthesizing a compound having the structure:

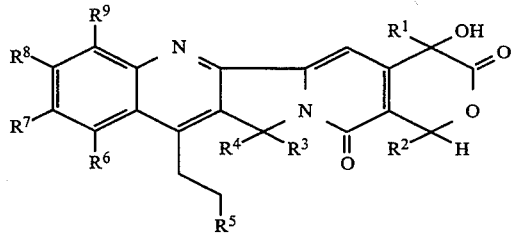

wherein R$^1$, R$^2$, R$^3$, and R$^4$ are independently the same or different and are H, or a linear or branched chain alkyl, alkylaryl, or hydroxyalkyl group, or an aryl group; R$^5$ is a linear or branched chain alkyl, alkylaryl, alkoxyalkyl, aryloxyalkyl, or hydroxyalkyl group, or an aryl group, or (CH$_2$)$_n$NR$^{11}$R$^{12}$, or (CH$_2$)$_n$OR$^{11}$; R$^7$ is OH, or a linear or branched chain alkyl, alkoxy, alkylaryl, or alkylaryloxy group, or an aryl group; R$^6$, R$^8$, and R$^9$, are independently the same or different and are H, or a linear or branched chain alkyl, alkylaryl, alkoxy, aminoalkoxy, or hydroxyalkyl group, or an aryl or aryloxy group, or nitro, CO$_2$R, Cl, F, Br, I, or SR$^{10}$; R$^{10}$, R$^{11}$ and R$^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, which comprises:

(a) treating an arylaldehyde having the structure:

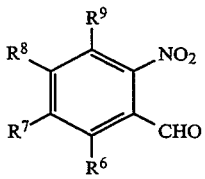

wherein $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, with a vinylic organometallic reagent having the structure:

R_5—CH=CH—M wherein $R^5$ is a linear or branched chain alkyl, alkylaryl, alkoxyalkyl, aryloxyalkyl, or hydroxy alkyl group, or an aryl group, or $(CH_2)_nNR^{11}R^{12}$, or $(CH_2)_nOR^{11}$, and M may be Li, K, Na, MgCl, and MgBr; to form a compound having the structure:

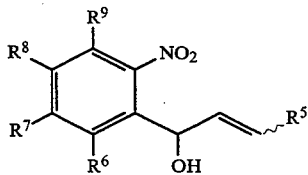

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; is an integer from 0 to 9;

(b) oxidizing the compound formed in step (a) with an oxidizing agent selected from the group comprising $CrO_3$, $K_2CrO_4$, and pyridinium dichromate to form a compound having the structure:

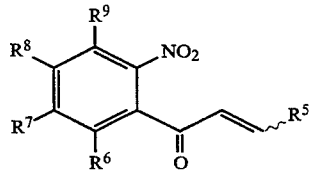

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9;

(c) reducing the compound formed in step (b) with a hydrogenating reagent comprising $H_2/PdC$, diimide, Wilkinson's reagent, and boron hydrides to form a compound having the structure:

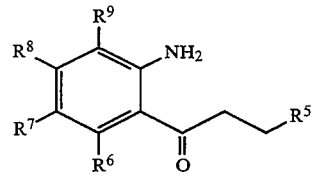

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9;

(d) condensing the compound formed in step (c) with a compound having the structure:

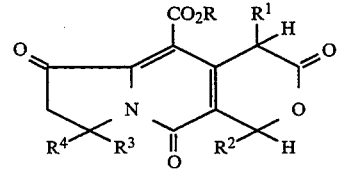

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; in the presence of an acid catalyst selected from the group comprising p-toluenesulfonic acid, benzenesulfonic acid, sulfuric acid, and hydrochloric acid to form a compound having the structure:

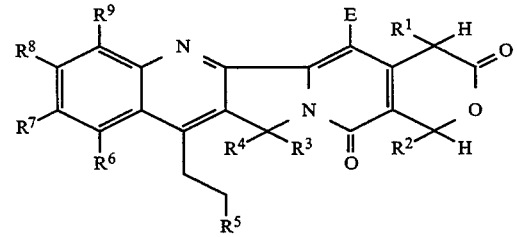

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^1$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9;

(e) hydrolyzing and decarboxylating the compound formed in step (d) using an acid selected from the group comprising hydrobromic acid, hydrochloric acid, and p-toluenesulfonic acid to form a compound having the structure:

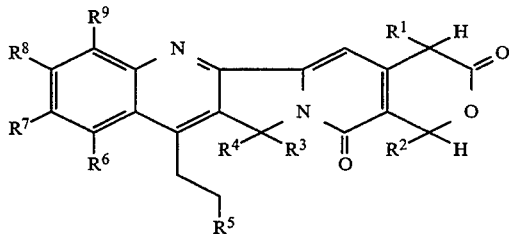

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxy alkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9; and, (f) treating the compound formed in step (e) with a hydroxylating reagent under suitable conditions to form a compound having the structure:

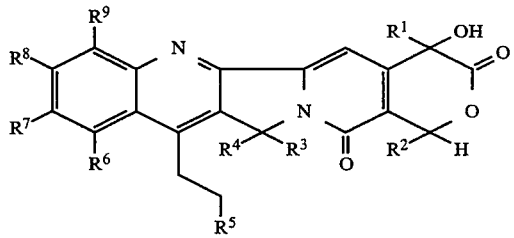

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxy alkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9. The hydroxylating reagent of the treating step (f), above, favorably comprises gaseous oxygen, cupric halide, and a base.

In one embodiment, the invention provides a process of synthesizing a compound having the structure:

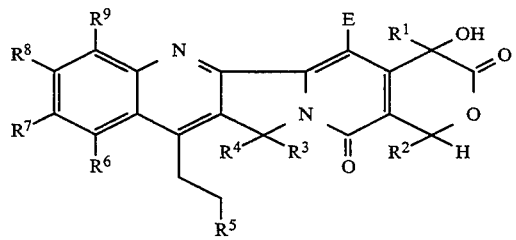

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, which comprises:

(a) preparing a compound having the structure:

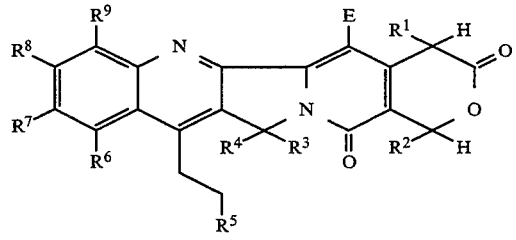

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxy alkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$, and $R^{12}$ are independently the same or different and are H, or a linear or branched chain alkyl, alkylaryl, hydroxy alkyl, or acyl group, or an aryl or glycosyl group; R is H, or a linear or branched chain alkyl, alkylaryl, or hydroxyalkyl group, or an aryl group; and, n is an integer from 0 to 9, as described above, and, (b) treating the compound prepared in step (a) with a hydroxylating reagent under suitable conditions to form a compound having the structure:

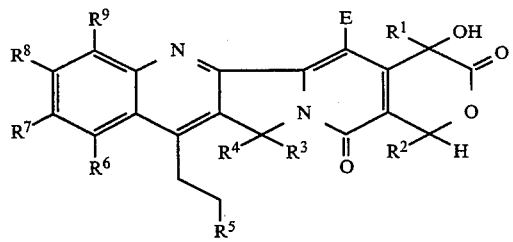

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9. The hydroxylating reagent of the treating step (b), above, favorably comprises gaseous oxygen, cupric halide, and a base.

In another embodiment, the invention provides a process of synthesizing a compound having the structure:

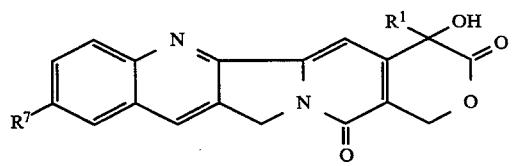

wherein $R^1$ is ethyl and $R^7$ is OH, which comprises:
(a) condensing a compound having the structure:

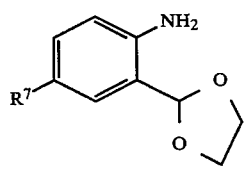

wherein $R^7$ is OH with a compound having the structure:

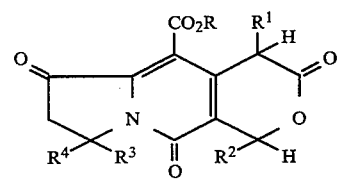

wherein R is H, or a linear or branched chain alkyl, alkylaryl, or hydroxyalkyl group, or an aryl group; $R^1$ is ethyl; $R^2$, $R^3$, and $R^4$ are H; and, $R^7$ is OR, with a suitable acidic catalyst comprising p-toluenesulfonic acid in toluene to form a compound having the structure:

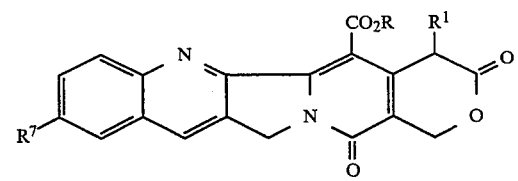

wherein R is H, or a linear or branched chain alkyl, alkylaryl, or hydroxyalkyl group, or an aryl group; $R^1$ is ethyl; and, $R^7$ is OR;

(b) hydrolyzing and decarboxylating the compound formed in step (a) with a suitable acid comprising hydrobromic acid to form a compound having the structure:

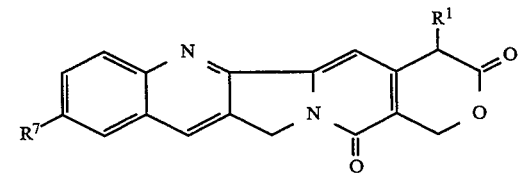

wherein $R^1$ is ethyl and $R^7$ is OR; and, (c) treating the compound formed in step (b) with a hydroxylating reagent under suitable conditions to form a compound having the structure:

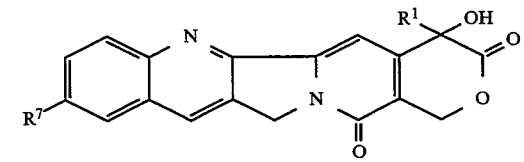

wherein $R^1$ is ethyl and $R^7$ is OH. The hydroxylating reagent of the treating step (c) favorably comprises gaseous oxygen, cupric halide, and a base.

In yet another embodiment, the invention provides a process of synthesizing a compound having the structure:

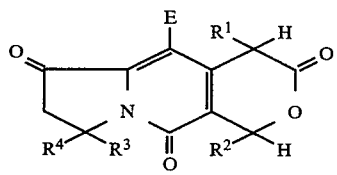

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) treating a compound having the structure:

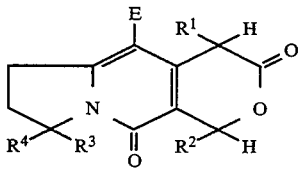

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; with a hydroxylating reagent under suitable conditions to form a compound having the structure:

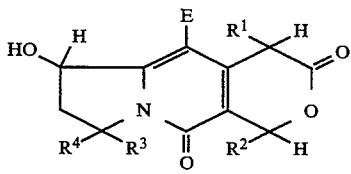

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) oxidizing the compound formed by step (a) with an oxidant under suitable conditions to form a compound having the structure:

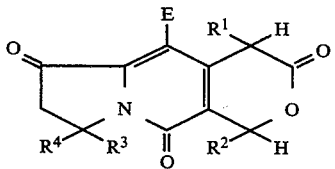

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group. The hydroxylating reagent of the treating step (a) favorably comprises gaseous oxygen, trialkyl phosphite, and sodium hexamethyldisilazide. The oxidant is favorably pyridinium dichromate.

The invention additionally provides a process of synthesizing a compound having the structure:

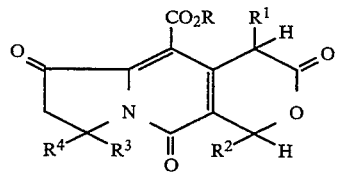

wherein R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) condensing an aryl aldehyde with a compound having the structure:

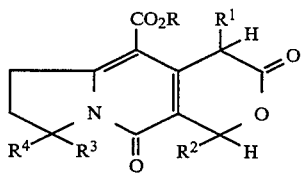

wherein R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, with a basic reagent under suitable conditions to form a compound having the structure:

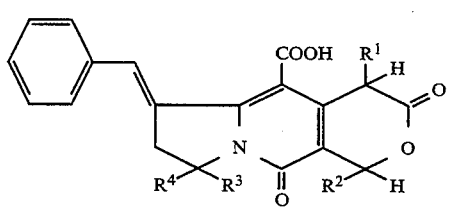

wherein R$^1$, R$^2$, R$^3$, and R$^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) ozonolyzing the compound formed by step (a) under suitable conditions to form a compound having the structure:

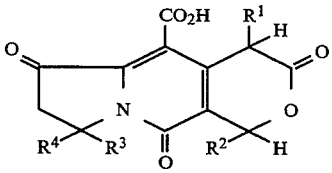

wherein R$^1$, R$^2$, R$^3$, and R$^4$ are independently the same or different and are H, or a linear or branched chain alkyl, alkylaryl, or hydroxyalkyl group, or an aryl group; and, (c) re-esterifying the compound formed in step (b) with a suitable reagent under suitable conditions to form a compound having the structure:

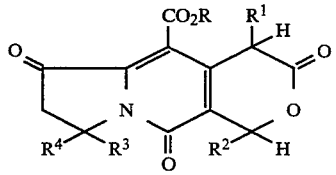

wherein R¹, R², R³, and R⁴ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group. The basic reagent of the condensing step (a) favorably comprises sodium hexamethyldisilazide. The reagent of re-esterifying step (c) is favorably trimethylsilyldiazomethane.

The invention also provides a process of synthesizing a compound having the structure:

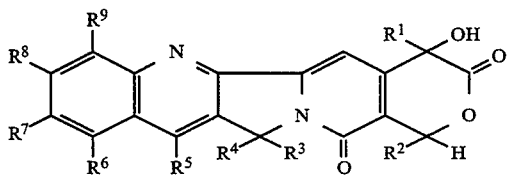

wherein R¹, R², R3, and R⁴ are independently the same or different and are H, or a linear or branched chain alkyl, alkylaryl, or hydroxyalkyl group, or an aryl group; R⁵ is a linear or branched chain alkyl, alkylaryl, alkoxyalkyl, aryloxyalkyl, or hydroxyalkyl group, or an aryl group, or (CH₂)$_n$NR¹¹R¹²; or (CH₂)$_n$OR¹¹; R⁷ is OH, or a linear or branched chain alkyl, alkoxy, alkylaryl, or alkylaryloxy group, or an aryl group; R⁶, R⁸, and R⁹ are independently the same or different and are H, or a linear or branched chain alkyl, alkylaryl, alkoxy, aminoalkoxy, or hydroxyalkyl group, or an aryl or aryloxy group, or nitro, CORR, Cl, F, Br, I, or SR¹⁰; R¹⁰, R¹¹ and R¹² are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, which comprises:

(a) preparing a compound as described hereinabove having the structure:

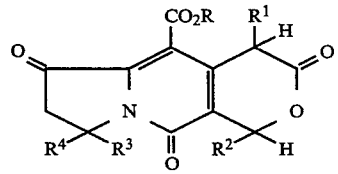

wherein R is H, or a linear or branched chain alkyl, alkylaryl, or hydroxyalkyl group, or an aryl group; R¹, R², R³, and R⁴ are independently the same or different and are H, or a linear or branched chain alkyl, alkylaryl, or hydroxyalkyl group, or an aryl group;

(b) condensing the compound formed in step (a) with a compound having the structure:

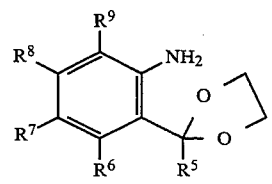

or

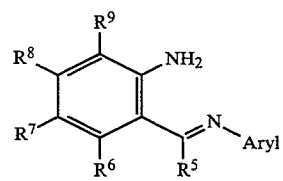

wherein R⁵ is a linear or branched chain alkyl, alkylaryl, alkoxyalkyl, aryloxyalkyl, or hydroxyalkyl group, or an aryl group, or (CH₂)$_n$NR¹R¹², or (CH₂)$_n$OR¹¹; R⁷ is OH, or a linear or branched chain alkyl, alkoxy, alkylaryl, or alkylaryloxy group, or an aryl group; R⁶, R⁸, and R⁹ are independently the same or different and are H, or a linear or branched chain alkyl, alkylaryl, alkoxy, aminoalkoxy, or hydroxyalkyl group, or an aryl or aryloxy group, or nitro, CO₂R, Cl, F, Br, I, or SR¹⁰; R¹⁰, R¹¹ and R¹² are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, under suitable conditions to form the compound having the structure:

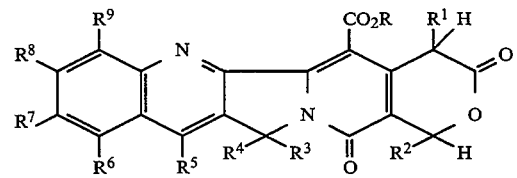

wherein R¹, R², R³, and R⁴ are independently the same or different and are H, or a linear or branched chain alkyl, alkylaryl, or hydroxyalkyl group, or an aryl group; R⁵ is a linear or branched chain alkyl, alkylaryl, alkoxyalkyl, aryloxyalkyl, or hydroxyalkyl group, or an aryl group, or (CH₂)$_n$NR¹¹R¹², or (CH₂)$_n$OR¹¹; R₇ is OH or a linear or branched chain alkyl, alkoxy, alkylaryl, or alkylaryloxy group, or an aryl group; R⁶, R⁸, and R⁹ are independently the same or different and are H, or a linear or branched chain alkyl, alkylaryl, alkoxy, aminoalkoxy, or hydroxyalkyl group, or an aryl or aryloxy group, or nitro, CO₂R, Cl, F, Br, I, or SR¹⁰; R¹⁰, R¹¹ and R¹² are independently the same or different and are H, or a linear or branched chain alkyl, alkylaryl, hydroxy alkyl, or acyl group, or an aryl or glycosyl group; R is H, or a linear or branched chain alkyl, alkylaryl, or hydroxyalkyl group, or an aryl group; and, n is an integer from 0 to 9;

(c) hydrolyzing and decarboxylating the compound formed in step (b) under suitable conditions to form a compound having the structure:

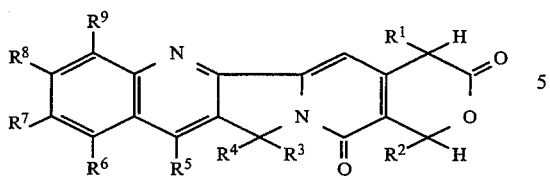

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH or a linear or branched chain alkyl, alkoxy, alkylaryl, or alkylaryloxY group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxy alkyl, or acyl group, or an aryl or glycosyl group; R is H, or a linear or branched chain alkyl, alkylaryl, or hydroxyalkyl group, or an aryl group; and, n is an integer from 0 to 9; and, (d) treating the compound formed in step (c) with a hydroxylating reagent under suitable conditions to form a compound having the structure:

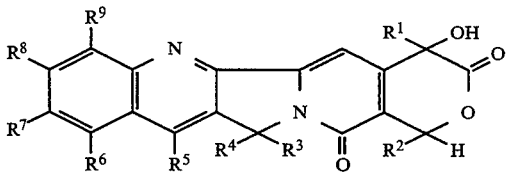

wherein $R^1$, $R^2$, $R^3$, and $R^4$ are independently the same or different and are H, or a linear or branched chain alkyl, alkylaryl, or hydroxyalkyl group, or an aryl group, $R^5$ is a linear or branched chain alkyl, alkylaryl, alkOxyalkyl, aryloxyalkyl, or hydroxyalkyl group, or an aryl group, or $(CH_2)_nNR^{11}R^{12}$, or $(CH_2)_n$; is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9. The hydroxylating reagent in step (d), above, favorably comprises gaseous oxygen, cupric halide, and a base.

The invention also provides a process of synthesizing a compound having the structure:

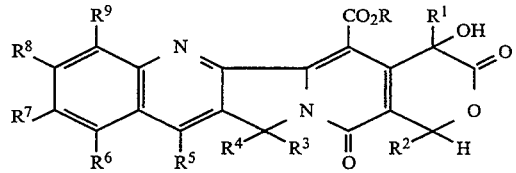

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, which comprises:

(a) preparing a compound as described hereinabove having the structure:

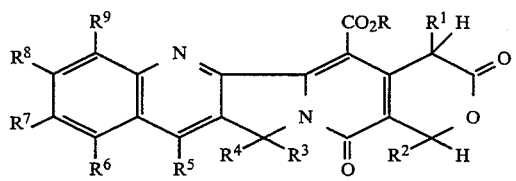

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9; and, (b) treating the compound formed in step (a) with a hydroxylating reagent under suitable conditions to form a compound having the structure:

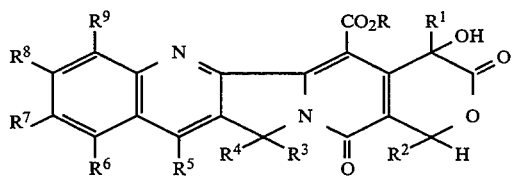

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9. The hydroxylating reagent in step (b), above, favorably comprises gaseous oxygen, cupric halide, and a base.

The invention also encompasses a process of synthesizing a compound having the structure:

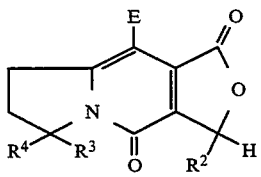

wherein E is H, $CO_2R$, $CONH_2$, CONHR, $CONR_2$, or CN; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9, which comprises:

(a) preparing a compound having the structure:

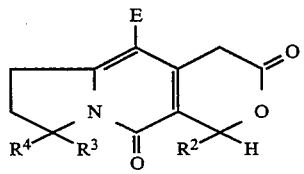

wherein E is H, $CO_2R$, $CONH_2$, CONHR, $CONR_2$, or CN; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9;

(b) treating the compound formed in step (a) with a hydroxylating reagent under suitable conditions to form a compound having the structure:

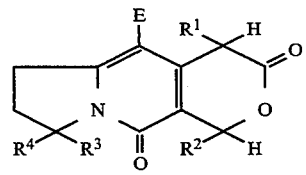

wherein E is H, $CO_2R$, $CONH_2$, CONHR, $CONR_2$, or CN; $R^1$ is OH; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9; and, (c) oxidizing the compound formed in step (b) with an oxidant under suitable conditions to form the compound having the structure:

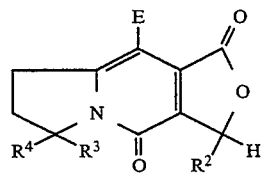

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group. The hydroxylating reagent in step (b) is favorably selenium dioxide. The oxidant in step (c) is favorably pyridinium dichromate.

In addition, the invention provides a process of synthesizing a compound having the structure:

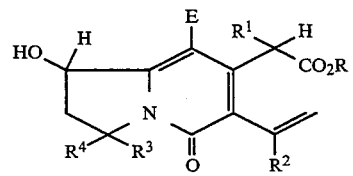

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyal.kyl group, or an aryl group; and, R is H, or a linear or branched chain alkyl, alkylaryl, or hydroxyalkyl group, or an aryl group, which comprises:

(a) preparing a compound having the structure:

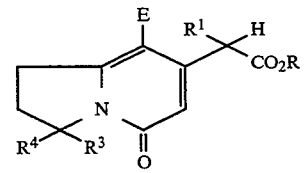

wherein E is H, $CO_2R$, $CONH_2$, CONHR, $CONR_2$, or CN; $R^1$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(b) reacting the compound formed in step (a) with a halogenating reagent to form a compound having the structure:

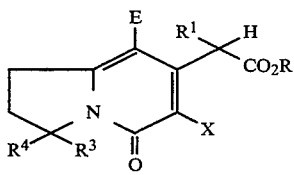

wherein X is Br, Cl, or I; E is H, CO$_2$R, CONH$_2$, CONHR, CONR$_2$, or CN; R$^1$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(c) cross-coupling the compound formed in step (b) with an organometallic reagent having the structure:

wherein M is a trialkylstannyl moiety and R$^2$ is H, or a linear or branched chain alkyl, alkylaryl, or hydroxyalkyl group, or an aryl group, under suitable conditions to form a compound having the structure:

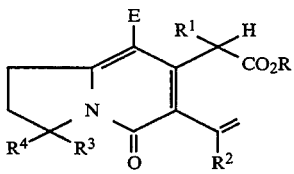

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group; and, (d) treating the compound formed in step (c) with a base and a hydroxylating reagent under suitable conditions to form a compound having the structure:

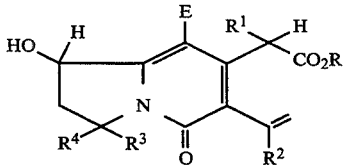

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group. The halogenating reagent in the reacting step (b) favorably comprises Br$_2$, Cl$_2$, or I$_2$. The organometallic reagent in the cross-coupling step (c) is favorably a vinyl tri-n-butylstannane. In a preferred embodiment, the base in the treating step (d) is potassium hexamethyldisilazide, and the hydroxylating reagent has the structure:

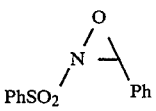

The invention provides a process of synthesizing a compound having the structure:

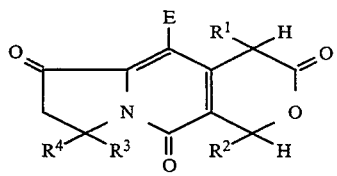

wherein E is H, CO$_2$R, CONHE, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group, which comprises:

(a) preparing as described hereinabove a compound having the structure:

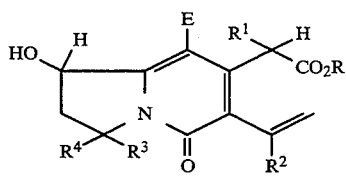

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(b) treating the compound formed in step (a) with an oxidative cleaving reagent under suitable conditions and with a hydride transfer reagent under suitable conditions to form a compound having the structure:

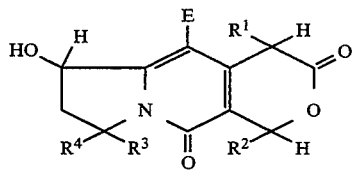

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group; and, (c) oxidizing the compound formed in step (b) with an oxidant under suitable conditions to form a compound having the structure:

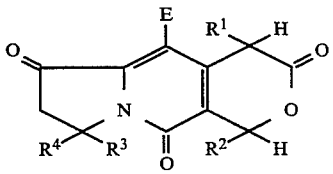

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group. The oxidative cleaving reagent in the treating step (b) is favorably ozone, and the hydride transfer agent therein is, in a preferred embodiment, lithium tri(t-butyloxy)boron hydride. The oxidant in the oxidizing step (c) is favorably pyridinium dichromate.

The invention further provides a process of synthesizing a compound having the structure:

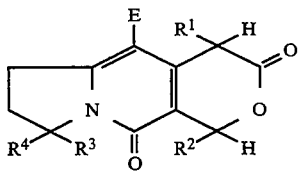

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group, which comprises:

(a) preparing a compound having the structure:

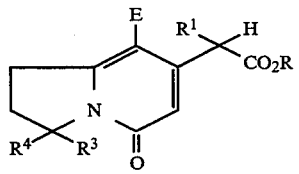

wherein E is H, CO$_2$R, CONH$_2$, CONHR, CONR$_2$, or CN; R$^1$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(b) treating the compound formed in step (a) with a basic reagent under suitable conditions to form a compound having the structure:

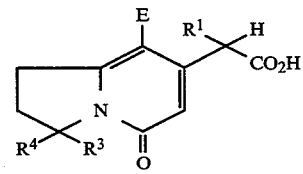

wherein E is H, CO$_2$R, CONH$_2$, CONHR, CONR$_2$, or CN; R is H, or a linear or branched chain alkyl, alkylaryl, or hydroxyalkyl group, or an aryl group; R$^1$, R$^3$, and R$^4$ are independently the same or different and are H, or a linear or branched chain alkyl, alkylaryl, or hydroxyalkyl group, or an aryl group; and, (c) condensing the compound formed in step (b) with an aldehyde R$^2$—CHO under suitable conditions to form a compound having the structure:

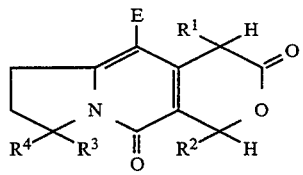

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group. The basic reagent is preferably potassium hydroxide. The aldehyde R$^2$—CHO is favorably formaldehyde.

BIOLOGICAL PROPERTIES

Cytotoxicity Assay

The synthesized compounds were evaluated for their cytotoxic effects on HL-60 (human promyelocytic leukemia) and 833K cells. The assay was conducted in 96-well microplates. The compounds were serially diluted in 4 to 6 steps with dimethylsulfoxide and added to cell incubation medium (RPMI 1640 containing 10% fetal cell serum) at the final concentration of 1.0% dimethylsulfoxide in the medium. The cytotoxicity of the compounds were determined by the XTT-microculture tetrazolium assay: 2′,3′-bis(2-methoxy-4-nitro-5-sulfophenyl)-3-[(phenylamino)carbonyl]-2H-tetrazolium hydroxide (XTT) was prepared at 1 mg/mL in prewarmed (37° C.) medium without serum. Phenazine methosulfate (PMS) and fresh XTT were mixed together to obtain 0.075mM PMS-XTT solution (25 mL of the stock with 5mg PMS added per 5 mL of I mg/mL XTT). Fifty microliters of this mixture were added to each well of the cell culture after 72 hours exposure to the testing compound. After incubation at 37° C. for 6 hours, the absorbance was determined at 450 nm and 630 nm with a microplate reader (EL 340, Bio-Tek Instruments, Inc., Winooski, Vt.). THe median-effect inhibitory concentration (IC$_{50}$) was determined from a medium-effect plot using computer software for the purpose.

The results of the assay of cytotoxicity towards HL-60 and 833K cells of several analogdes of camptothecin prepared in accord with the invention are illustrated in the accompanying Tables I and II, along with comparison data for native camptothecin. The data shown indicate that the camptothecin analogdes prepared by the new methods provided by the invention have significant cytotoxic activity against cancer cells. The data shown indicate that the new camptothecin analogues have significant cytotoxic activity against cancer cells.

The present invention therefore provides a method of treating cancer, which comprises administering an anti-cancer-effective quantity of any of the analogues of camptothecin disclosed herein. The drug may be administered to a patient afflicted with cancer by any conventional route of administration, including, but not limited to, intravenous, intramuscular, oral, subcutaneous, intratumoral, intradermal, and parenteral. The anticancer-effective quantity is between 0.01 mg and 10.0 mg per kg of subject body weight.

The present invention also provides a pharmaceutical composition comprising any of the analogues of camptothecin disclosed herein and a pharmaceutically acceptable carrier. The composition may contain between 1 mg and 500 mg of a camptothecin analogue, and may be constituted into any form suitable for the mode of administration selected. Compositions suitable for oral administration include solid forms, such as pills, capsules, granules, tablets, and powders, and liquid forms, such as solutions, syrups, elixers, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectible medium. Carriers are intended to include necessary and inert binders, suspending agents, lubricants, flavorants, sweeteners, preservatives, dyes, and coatings.

Optimal dosages to be administered may be determined by those skilled in the art, and will vary with the particular camptothecin analogue in use, the strength of the preparation, the mode of administration, and the advancement of the disease condition. Additional factors depending on the particular patient being treated will result in a need to adjust dosages, including patient age, weight, gender, diet, and time of administration.

TABLE 1

CYTOTOXICITY OF CAMPTOTHECIN AND DERIVATIVES ON HL60 CELL AND 833K CELL GROWTH DURING 72 HR EXPOSURE, USING XTT ASSAYS

| Compound[a] | TopoI Relaxation | TopoI DNA Cleavage | Inhibitory Concentrations | | | | | |
|---|---|---|---|---|---|---|---|---|
| | | | HL-6 | | | 833K | | |
| | | | $IC_{50}$ | $IC_{70}$ | $IC_{95}$ | $IC_{50}$ | $IC_{70}$ | $IC_{95}$ |
| WS-1 (CPT) Camptothecin | ++++ | +++ | 0.094 0.0035 | 0.012 0.006 | 0.025 0.022 | +0.004 0.0153 | +0.004 0.043 | 0.649 ±0.160 |
| WS-2 (20-deoxy-CPT) 20-Deoxycamptothecin | +++ | ++ | 0.039 | 0.052 | 0.109 | 0.0096 0.310+ | ±0.023 0.143 | 3.17 + 1.01 |
| WS-3 (14-carbomethoxy-20-deoxy CPT) 14-Carbomethoxy-20-deoxycamptothecin | +++ | + | 0.914 | 0.318 | 1.082 | >50 | | |
| WS-4 (14-carbomethoxy-20-deoxy CPT) 14-Carbomethoxy-20-deoxycamptothecin | ++ | — | 2.44 | 12.0 | 618.7 | +0.287 2.263 | +0.820 5.80 | 59.8 ±11.7 |
| WS-5 (14-carbomethoxy-CPT) 14-Carbomethoxy-Campotothecin | + | ± | >5 | — | — 63.5+ | 28.3 | 83.7 | 898 ± 750 |
| WS-6 (17-methyl-CPT) 17-Methylcamptothecin | ++ | | 0.266 | 0.432 | 1.432 | 0.254 3.17+ | +0.34 7.34 | 40.1± 0.689 |
| WS-7 (20-methyl-CPT) 20-Methylcamptothecin | ++++ | | 0.062 | 0.090 | 0.229 | +0.034 0.082 | 0.290 ±0.05 | 7.16± 2.84 |
| WS-8 20-dehydrated-CPT | + | | 3.44 | 5.47 | 17.14 | +0.250 1.70 | 4.75 ±0.092 | 50.4 ± 13.8 |
| 11-Isotopotecan | +++ | | >5 | — | — | >500 | | |

[a]All Compounds were dissolved in DMSO and heated to 56° C. prior to serial dilution with DMSO.

TABLE II

CYTOTOXICTY OF CAMPTOTHECIN AND DERIVATIVES ON HL-60 CELL GROWTH DURING 72 HR EXPOSURE, USING XTT ASSAYS

| Compound[b] | Topo I Relaxation | TopoI DNA Cleavage | Inhibitory Concentrations (μM) | | |
|---|---|---|---|---|---|
| | | | $IC_{50}$ | $IC_{70}$ | $IC_{95}$ |
| WS-1 (CPT) Camptothecin | ++++ | +++ | 0.0094 0.0035 | 0.012 0.006 | 0.025 0.022 |
| WS-2 (20-deoxy-CPT) 20-Deoxycamptothecin | +++ | ++ | 0.039 | 0.052 | 0.109 |
| WS-3 (14-carbomethoxy-20-deoxy CPT) 14-Carbomethoxy-20-deoxycamptothecin | +++ | + | 0.194 | 0.318 | 1.082 |
| WS-4 (14-carbomethoxy-20-deoxy CPT) 14-Carbomethoxy-20-deoxycamptothecin | ++ | — | 2.44 | 12.0 | 618.7 |
| WS-5 (14-carbomethoxy-CPT) 14-Carbomethoxy-Camptothecin | + | ± | >5 | — | — |
| WS-6 (17-methyl-CPT) 17-Methylcamptothecin | ++ | | 0.266 | 0.432 | 1.432 |
| WS-7 (20-methyl-CPT) 20-Methytcamptothecin | ++++ | | 0.062 | 0.090 | 0.229 |
| WS-8 | + | | 3.44 | 5.47 | 17.14 |

TABLE II-continued

CYTOTOXICTY OF CAMPTOTHECIN AND
DERIVATIVES ON HL-60 CELL GROWTH
DURING 72 HR EXPOSURE, USING XTT ASSAYS

| Compound[b] | Topo I Relaxation | TopoI DNA Cleavage | Inhibitory $IC_{50}$ | Concentrations ($\mu$M) $IC_{70}$ | $IC_{95}$ |
|---|---|---|---|---|---|
| 20-dehydrated-CPT 11-Isotopotecan | +++ | >5 | — | — | |
| Topotecan (844K cells) | | | 0.046 | — | — |

[b]All compounds were dissolved in DMSO and heated to 56° C. prior to several dilution with DMSO.

The following Experimental Details are set forth to aid in an understanding of the invention, and are not intended, and should not be construed, to limit in any way the invention set forth in the claims which follow thereafter.

Experimental Details

General

All air and moisture sensitive reactions were performed in a flame-dried apparatus under a nitrogen atmosphere unless otherwise noted. Air-sensitive liquids and solutions were transferred via syringe or cannula. Unless otherwise noted, all solvents and reagents were commercial grade and were used as sold. The following are exceptions, and are all distilled under nitrogen using the drying methods listed in parentheses: dichloromethane (calcium hydride), benzene (calcium hydride), tetrahydrofuran (sodium/benzophenone ketyl), diethyl ether (sodium/benzophenone ketyl), diisopropylamine (calcium hydride).

Melting points (mp) were uncorrected and performed in soft glass capillary tubes using an Electrothermal series IA9100 digital melting point apparatus. Infrared (IR) spectra were obtained with a Perkin-Elmer 1600 Series Fourier Transform Spectrometer. Samples were prepared as neat films on NaCl plates unless otherwise noted. Proton nuclear magnetic resonance (1H NMR) spectra were determined using a Bruker AMX-400 spectrometer operating at 400 MHz. Carbon nuclear magnetic resonance (13C NMR) spectra were obtained on a Bruker AMX-400 spectrometer operating at 100 MHz with composite pulse decoupling.

High resolution mass spectra (HRMS) were determined by electron impact ionization (EI) on a JEOL JMS-DX 303HF mass spectrometer with perfluorokerosene (PFK) as an internal standard.

Flash chromatography was carried out on silica gel according to the protocol of Still (W. C. Still, et al., *J. Org. Chem,*, 43, 2923 (1978)).

EXAMPLE 1

2-Methoxypyrroline

To the stirring neat dimethyl sulfate (265.0 g, 2.1 mol) was added dropwise 2-pyrrolidinone (170 g, 2.00 mol) over 2 h. The reaction was then heated at 60° C. for 16 h. After cooling the reaction to room temperature, it was poured onto ice (500 g) mixed with potassium carbonate (300 g). The organic layer was separated and the aqueous layer was extracted with ether (3×100 mL). The combined organic layer and extracts were dried over anhydrous magnesium sulfate, filtered, and concentrated under vacuum (the bath temperature was kept under 20° C.). The resulting solution was distilled under vacuum to give 156 4 g (37°–40° C. 74 torr), which was redistilled at 115°–120° C. under atmosphere to give of the desired product (129 g, 65%). 1H NMR (400 MHz, CDCl3) 3.80 (s, 3 H),3.65(tt, J=1.2, 7.1 Hz, 2H), 2.43 (tt, J=1.2, 7.4 Hz, 2H), 2.02 (m, 2H). 13C NMR (100 MHz, CDCl3) 10.10 (brs, 1H), 3.73 (t, J=7.6 Hz, 2H),3.39 (t, J=8.0 Hz, 2 H), 2.16 (quintet, J=7.7 Hz, 2H), 1.68 (s,6H).

EXAMPLE 2

IsoproDylidene α-(Tetrahydro-2-pyrrolidene)malonate (3)

A solution of 2 (55.8 g, 0.563 mol), Meldrum's acid (81.1 g, 0.563 mol) and triethylamine (10 mL) in benzene (300 mL) was refluxed 10 h. The solid residue after evaporation of the reaction mixture was recrystallized from absolute ethanol to give the desired product 3 as white crystals (110.0 g, 92.5%). 1H NMR (400 MHz, CDCl3) δ 10.10 (brs, 1H), 3.73 (t, J=7.6 Hz, 2H), 3.39 (t, J=8.0 Hz, 2H), 2.16 (quintet, J=7.7 Hz, 2H), 1.68 (s, 6H).

EXAMPLE 3

2-Carbomethoxymethylenepyrroline (4)

To the solution of 3 (42.2 g, 200 mmol) in anhydrous methanol (200 mL) was added a solution of sodium methoxide in methanol (25% w/w, 47.5 g, 220 mmol), and the resulting solution was refluxed 2 h. The reaction mixture was concentrated under vacuum to a semi solid before iced water (200 mL) was added to it. The resulting solution was adjusted to pH 5–6 by 2N HCl, and extracted with methylene chloride (5×100 mL). The combined extracts was dried over anyhydrous magnesium sulfate, filtered, and concentrated to give yellow solid. Recrystallization of the residue solid from hexane afforded the desired product as pale yellow solid (27.6 g, 97.7%). 1H NMR (400 MHz, CDCl3) 7.88 (brs, 1 H),4.53(s, 1H), 3.62 (s,3H0, 3.51 (t,J=6.9 Hz, 2H), 2.57 (t,J=7.7 Hz, 2 H), 1.96 (quintet, J=Hz, 2H). 13C NMR (100 MHz, CDCl3) 171.0, 166.6, 76.2, 50.0, 47.0, 32.2, 22.0 ppm. IR (neat) 3365, 2948, 2881, 1652, 1603, 1501, 1237, 1146, 1064, 777cm$^{-1}$.

EXAMPLE 4

3-Carbomethoxymethyl-4-carbomethoxy-1,6-cyclopentano-2-pyridone (6)

To the solution of 4 (27.6 g, 195 mmol) in absolute ethanol (200 mL) was added dimethyl 1,3-allenyldicarboxylate 514 (33.6 g, 215 mmol) and triethylamine (2 mL). The reaction was stirred at room temperature for 65 h. The reaction mixture was concentrated to near dryness. Trituration of the residue with dry ether (50 mL) afforded 6 as a white solid (47.8 g, 92.3%). 1H NMR (400 MHz, CDCl3) δ6.21 (s, 1H), 4.11 (t, J=7.4 HZ, 2H), 3.74 (s, 3H), 3.73 (s, 2H), 3.66 (s, 3H), 3.44 (t, J=7.9 Hz, 2H), 2.16 (quintet, J=7.6 Hz, 2H). 13C NMR (100 MHz, CDCl3) δ 170.9, 165.8, 161.0, 157.4, 147.1, 120.1, 106.5, 52.1, 51.6, 49.1, 41.1, 34.7, 20.6 ppm. IR (neat) 2953, 1734, 1716, 1656, 1520, 1436, 1294, 1203 cm$^{-1}$.

EXAMPLE 5

3-(1-Carbomethoxypropyl)-4-carbomethoxy,-1,6-cyclopentano-2-pyrridone (7)

To a solution of pyridone 6 (47.0 g, 177 mmol) in anhydrous dimethoxyethane (700 mL) at −78° C. was added potassium t-butoxide (20.8 g, 186 mmol). After 20 min ethyl iodide (50.3 g, 354 mmol) was added and the solution was allowed to warm to room temperature and stirred for 30 h. The reaction mixture was then poured to brine (300 mL) and the aqueous layer extracted with methylene chloride (4×200 mL). The combined organic phase and the extracts was dried over anhydrous magnesium sulfate, filtered, and concentrated. The semisolid residue was then recrystallized from ethyl acetate to give 7 as a pale yellowish green solid (36.54 g, 2 crops). The mother liquid was subjected to flash chromatography with ethyl acetate to afford more product (11.2 g, total yield 91.0%). $^1$H NMR (400 MHz, CDCl$_3$) δ 6.35 (s, 1H), 4.13 (dt, J=1.2, 7.5 Hz, 2H), 3.99 (t, J=7.2 Hz, 1H), 3.80 (s, 3H), 3.64 (s, 3H), 3.39 (dt, J=2.6, 8.0 Hz, 2H), 2.17 (quintet, J=7.6 Hz, 2H), 2.05 (m, 1H), 0.91 (t, J=7.4 Hz, 3H). $^{13}$C NMR (100 MHz, CDCl3) δ 173.0, 166.1, 161.1, 156.3, 151.6, 117.2, 107.0, 53.1, 51.7, 49.8, 49.2, 34.5, 25.4, 20.7, 12.4 ppm. IR (neat) 2959, 2919, 1714, 1710, 1668, 1585, 1516, 1437, 1352, 1273, 1193, 1094, 1032, 976.3 cm$^{-1}$.

EXAMPLE 6

14-Carbomethoxy-de-AB-deoxycamptothecin (8)

A mixture of 7 (5.01 g, 17.1 retool), formaldehyde (3.08 g), concentrated sulfuric acid (1 mL) and water (1 mL) in dioxane (25 mL) and extracted with methylene chloride (4×50 mL). The combined extracts was dried over anhydrous magnesium sulfate, filtered, and concentrated to a pale yellow sticky oil 8 which was already pure as shown by $^1$H NMR. Thr product was used directly for the next step. 1H NMR (400 MHz, CDCl$_3$) δ 5.48 (d, J=5.8 Hz, 1H), 5.13 (d, J=5.8 Hz, 1H), 4.34 (dd, J=5.1, 9.1 Hz, 1H), 4.19, (dt, J=2.9, 7.6 Hz, 2H), 3.85, (s, 3H), 3.48 (dt, J=3.6, 7.9 Hz, 2H), 2.22 (quintet, J=7.6 Hz, 2H), 1.65-2.01 (m, 2H), 1.08 (t, J=7.6 Hz, 3H). $^{13}$C NMR (100 MHz, CDCl$_3$) δ 171.3, 165.2, 157.9, 167.0, 147.3, 118.5, 104.9, 65.0, 52.0, 49.5, 44.3, 34.8, 25.3, 20.7, 11.9 ppm. IR (neat) 2925, 1734, 1713, 1650, 1548, 1440, 1309, 1170, 1097, 1047 cm$^{-1}$.

EXAMPLE 7

De-AB-deoxycampothecin (9)

A mixture of 8 in aqueous hydrobromic acid (48%, 50 mL) was heated at 105° C. for 18 h. It was then poured into brine (60 mL) and extracted with methylene chloride (4×50 mL). The combined extracts was dried over anhydrous magnesium sulfate, filtered, and concentrated. The residue was then subjected to flash chromatography with 50:50:1 chloroform/ethyl acetate/methanol to afford 9 as an off-white solid (2.11 g, 52.9%). $^1$H NMR (400 MHz, CDCl$_3$) δ 5.98 (s, 1H), 5.38 (d, J=5.7 Hz, 1H), 5.20 (d, J=5.7 Hz, 1H), 4.12 (t, J=7.3 Hz, 2H), 3.35 (t, J=6.6 Hz, 1H), 3.08 (t, J=7.7 Hz, 2H), 2.21 (quintet, J=7.74 Hz, 2H), 1.80-1.98 (m, 2H), 0.99 (t, J=7.4 Hz, 3H). $^{13}$C NMR (100 MHz, CDCl$_3$) δ 171.4, 158.5, 150.5, 146.6, 117.2, 100.2, 66.1, 48.6, 45.8, 31.8, 25.1, 21.5, 11.3 ppm.

EXAMPLE 8

2-Hydroxy-de-AB-campothecin (10)

A mixture of 9 (778 mg, 3.33 mmol), selenium dioxide (1.85 g, 16.7 mmol) in wet dioxane (95%, 20 mL) in a sealed tube was heated at 155° C. for 4 h. It was then poured into water and extracted with methylene chloride (4×30 mL). The combined extracts was dried over anhydrous magnesium sulfate, filtered, and concentrated. The dark solid residue was then chromatographed with 25% acetone in chloroform (300 mL) and 30:20:1 chloroform/acetone/methanol (500 mL) to afford 10 as a yellowish solid (377.4 mg, 42.7%). The diastereomeric ratio is about 1:1. $^1$H NMR (400 MHz, DMSO-d$_6$ with 1 small drop of D$_2$O) δ 6.51 (s, 1H), 5.25 (dd, J=15.4, 19.0 Hz, 2H), 5.13 (t, J=7.0 Hz, 1H), 4.08 9, 1H), 2.42 (m, 1H), 1.93 (m, 1H), 1.76 (m, 2H), 0.82 (t, J=7.1 Hz, 3H). $^{13}$C NMR (100 MHz, DMSO-d$_6$) δ 172.59, 172.54, 156.87, 152.94, 152.90, 149.83, 149.78, 116.33, 97.37, 72.09, 72.04, 71.94, 65.16, 59.68, 45.62, 31.25, 31.19, 30.30, 30.26, 7.66 ppm (21 peaks observed). HRMS calculated for C$_{13}$H$_{15}$NO$_5$ (M+) 265.0950, observed 265.0952.

EXAMPLE 9

2-Oxo-de-AB-camptothecin (11)

To the suspension of 10 (356.1 mg, 1.34 mmol) and 4 Å molecular sieves (activated powder, 1.50 g) in methylene chloride (15 mL) at 0° C. was added pyridinium dichoromate (1.01 g. 2.68 mmol). After 3.5 h, 30 mL ethyl acetate was added to the mixture, and it was filtered through a plug of silica gel and celite. The residue after evaporation of the filtrate was flash chromatographed with 1:1 chloroform/ethyl acetate to give 11 (159.6 mg, 45.2%). $^1$H NMR (400MHz, CDCl$_3$) δ 7.23, (s, 1H), 5.68, (d, J=7.1 Hz, 1H), 5.25, (d, J=7.1 Hz, 1H), 4.35 (t, J=6.8 HZ, 2H), 3.65 (s, 1H, from the OH), 2.97 (t, J=6.8 Hz, 2H), 1.82 (m, 2H), 0.99 (t, J=7.4 Hz, 3H). $^{13}$C NMR (100 MHz, CDCl$_3$) δ 196.0, 173.3, 157.7, 149.3, 139.9, 124.5, 100.8, 72.3, 66.3, 42.2, 33.7, 31.8, 7.7 ppm. HRMS calculated for C$_{13}$H$_{13}$NO$_5$ (M+) 263.0794, observed 263.0809.

EXAMPLE 10 dl-Camptothecin (1)

A suspension of 11 (185.2 mg, 0.704 mmol) and 12 (178 mg, 0,844 mmol; W. Borsche, et al., Chem. Ber., 76, 1099 (1943)) in toluene (20 mL) was refluxed for 0.5h. Then, toluenesulfonic acid monohydride (10 mg) was added, and the reaction was refluxed with a Dean-Starr trap for 3.5 h. The raction was cooled to room temperature and most solvent was evaporated in vacuum. The residue was flash chromotographed with 100:10:1 chloroform/acetonitrile/methanol to give 196.5 mg (80.3%) brown-yellow solid. Recrystallization with 10% methanol in chloroform giave 173.1 mg off-white solid, m.p. 264°-265° C. (dec). $^1$H NMR (400 MHz, DMSOOd$_6$) δ 8.70 (s, 1 H), 8.16 (m, 2H), 7.88 (t, J=7.5 Hz, 1H), 7.72 (t, J=Hz, 1H), 7.36 (s, 1H), 6.54 (s, 1H), 5.43 (s, 2H), 5.30, (s, 1H), 1.87 (m, 2H), 0.88 (t, J=7.0 Hz). $^{13}$C NMR (100 MHz, CDCl$_3$) δ 172.4, 156.8, 149.9, 147.9, 145.4, 131.6, 130.3, 129.8, 129.0, 128.4, 127.9, 127.6, 119.0, 96.6, 72.3, 65.2, 50.2, 30.2, 7.7 ppm (19 peaks observed). HRMS (FAB) calculated for C$_{20}$H$_{16}$N$_2$O$_4$ (M+1)+ 349.1188, observed 349.1184.

EXAMPLE 11

14-Carbomethoxy-2-hydroxy-de-AB-deoxycamptothecin (14)

To a solution of 8 (1.20 g, 4.12 mmol) in THF (20 mL) at −78° C. was added KHMDS (1.9 g, 9.06 mmol) in THF (10 mL) and Davis' oxazirdine (1.05 g, 4.04 mmol) in THF (10 mL) simultaneously over 20 min. A solution of saturated ammonium chloride (10 mL) was added to the reaction mixture in 10 min, and the reaction was left to warm up to room temperature. The reaction mixture was poured into a brine solution, and the aqueous phase was extracted with chloroform (30 mL×3). The combined organic phase and the extracts were dried over anhydrous magnesium sulfate, filtered, and concentrated. The residue was then loaded onto a flash column, eluted with 30% ethyl acetate in chloroform (500 mL) and 15% acetone in chloroform (1500 mL) to give 15 (246 mg, 19%) and the desired secondary alcohol 14 (707 mg, 56%) as a mixture of diastereomers (1.3:1 ratio from integration of $^1$HNMR.) $^1$H NMR (400 MHz, CDCl$_3$) δ 5.40–5.52 (m, 3H), 5.10 (m, 2H), 4.42 & 4.05 (1H), 4.24 (m, 2H), 3.90 (s, 3H), 2.31 (m, 2H), 1.70–1.91 (m, 2H), 1.09 & 0.98 (2t's, J=7.3 Hz, 3H). IR (neat) 3390, 2958, 1732, 1651, 1556, 1435, 1306, 1157, 1090, 748 cm$^{-1}$.

EXAMPLE 12

14-Carbomethoxy-2-oxo-de-AB-deoxycamptothecin (16)

A mixture of 14 (595 mg, 1.94 mmol), PDC (2.18 g, 5.80 mmol) and activated 4 Å molecular sieve powder (2.20 g) in methylene chloride (20 mL) was stirred at 0°–5° C. for 4 h. It was then diluted with ethyl acetate (30 mL) and filtered through celite. The flask and the residue was rinsed and washed with 50% ethyl acetate in chloroform (20 mL×5 ) and the filtrate was concentrated in vacuum to give pure 16 (490.2 mg, 83%). $^1$H NMR (400 MHz, CDCl$_3$) δ 5.55 (d, J=17.2 Hz, 1H), 5.24 (d, J=17.2 Hz, 1H), 4.32 (t, J=6.8 Hz, 2H), 3.93 (s, 3H), 3.68 (dd, J=5.2, 8.6 Hz, 1H), 2.97 (t, J=6.8 Hz, 2H), 2.01 (m, 1H), 1.80 (m, 1H), 1.04 (t, J=7.4 Hz, 3H). $^{13}$C NMR (100 MHz, CDCl$_3$) δ 194.3, 169.5, 164.0, 157.2, 144.6, 137.7, 126.4, 110.2, 65.7, 53.4, 43.6, 42.2, 33.7, 26.1, 11.5 ppm. IR (neat) 2952, 1742, 1658, 1614, 1440, 1300, 1159, 1057 cm$^{-1}$.

EXAMPLE 13

14-Carbomethoxy-deoxycamptothecin (17)

A solution of 16 (601 mg, 0.197 mmol) and 12 (497 mg, 2.36 mmol) in toluene (20 mL) was refluxed for 40 min. Then toluenesulfonic acid monohydrate (20 mg) was added, and the reaction flask was equipped with a Dean-Stark trap. Reflux was continued for 4 h before the reaction was cooled to room temperature. It was concentrated to about 10 mL via vacuum, and filtered. The solid thus obtained was recrystallized from chloroform to give 17 (578 mg 75%), m.p. 300°–302° C. (dec) $^1$H NMR (400 MHz, CDCl$_3$) δ 8.38 (s, 1H), 8.11 (d, J=8.4 Hz, 1H), 7.91 (d, J=8.2 Hz, 1H), 7.81 (dr, J=1.2, 7.7 Hz, 1H), 7.66 (t, J=7.5 Hz, 1H), 5.62 (d, J=16.2 Hz, 1H), 5.30 (d, J=16.2 Hz, 1H), 5.28 (s, 2H), 4.12 (s, 3H), 3.78 (dd, J=5.2, 8.7 Hz, 1H), 2.12 (m, 1H), 1.93 (m, 1H), 1.11 (t, J=7.4 Hz, 3H). $^{13}$C NMR (100 MHz, CDCl$_3$) δ 170.2, 165.6, 157.2, 151.4, 148.8, 145.1, 144.4, 130.9, 130.6, 130.3, 128.53, 128.48, 128.04, 127.99, 120.5, 108.3, 65.7, 52.9, 50.2, 44.1, 26.0, 11.6 ppm. HRMS calculated for $C_{22}H_{18}N_2O_5$ (M+) 390.1216, observed 390.1231.

EXAMPLE 14

Deoxycamptothecin (18)

A solution of 17 (207.5 mg, 0.531 mmol) in 48% aqueous hydrobromic acid (8 mL) in a sealed tube was heated for 15 h at 140° C. After it was cooled, the reaction mixture was concentrated to near dryness via vacuum. The mixture was then carefully neutralized with sodium hydroxide; 2N) and saturated sodium bicarbonate to pH 6–8. The aqueous mixture was extracted with chloroform (15 mL×10). The combined extracts were dried over anhydrous magnesium sulfate, filtered, and concentrated. The residue was flash chromotographed with 2% methanol in chloroform to give be (124.3 mg, 71%). HRMS calculated for $C_{20}H_{16}N_2O_3$ (M+) 332.1161, observed 332.1151.

EXAMPLE 15 dl-Camptothecin (1)

To a solution of 18 (47.8 mg, 0.144 mmol), copper(II) chloride (80 mg) and dimethylamine (100 μl ) in DMF (16 mL) was bubbled in oxygen for 7 h. The reaction mixture was concentrated in vacuum to about 5 mL, and was then diluted with water. A solution of saturated ammonium chloride was used to adjusted the pH of the above mixture to about 6, and the resulting mixture was extracted with chloroform (10 mL×10). The combined extracts were dried over anhydrous magnesium sulfate, filtered, and concentrated. The residue was flash chromatographed with 2% methanol in chloroform to give dl-camptothecin (45.5 mg, 91%).

EXAMPLE 16

4-Carbomethoxymethyl-5-carbomethoxy-1,6-cyclopentano-2-pyridone (6)

To the solution of enamine 4 (27.6 g, 195 mmol) in absolute ethanol (200 mL) was added dimethyl3-chloroglutaconate (Org. Syn. Coll. Vol. VI, 505); 41.3 g, 215 mmol) and triethylamine (32 mL, 230 mmol). The reaction was stirred at room temperature for 65 h. The reaction mixture was concentrated to near dryness. Trituration of the residue with dry ether (50 mL) afforded 6 as a white solid (47.8 g, 92%). $^1$H NMR (CDCl$_3$) ≠ 6.21 (s, 1 H), 4.11 (t, J=7.4 Hz, 2 H), 3.74 (s, 3 H), 3.73 (s, 2 H), 3.66 (s, 3 H), 3.44 (t, J=7.9 Hz, 2 H), 2.16 (quintet, J=7.6 Hz, 2H). $^{13}$C NMR (CDCl$_3$) δ 170.9, 165.8, 161.0, 157.4, 147.1. 120.1, 106.5, 52.1, 51.6, 49.1, 41.1, 34.7, 20.6. IR (neat) 2953, 1734, 1716, 1656, 1652, 1520, 1436, 1294, 1203 cm$^{-1}$.

EXAMPLE 17

4-(1-Carbomethoxypropyl)-5-carbomethoxy-1,6-cyclopentano-2-pyridone (7)

To a solution of pyridone 6 (47.0 g, 177 mmol) in any DME (700 mL) at −70° C. was added potassium tert-butoxide (20.8 g, 186 mmol). After 20 rain, EtI (50.3 g, 354 mmol) was added and the solution was allowed to warm to room temperature and stirred for 30 h. The reaction mixture was then poured to brine (300 mL) and the aqueous layer extracted with $CH_2Cl_2$ (4×200 mL). The combined organic phase and the extracts were dried (MgSO$_4$), filtered and concentrated. The semi-solid residue was then recrystallized (EtOAc) to give 7 as pale yellow-green sold (36.54 g, 2 crops). The mother liquor was subjected to flash chromatography with ethyl acetate to afford an additional 11.2 g (total yield of 91%), m.p. 92.5°–94.0 ° C. $^1$H NMR (CDCl$_3$) δ 6.35 (s, 1 H), 4.13 (dt, J=1.2, 7.5 Hz, 2 H), 3.99 (t, J=7.2 Hz, 1 H), 3.80 (s, 3H), 3.64 (s, 3 H), 3.39 (dt, J=2.6, 8.0 Hz, 2 H), 2.17 (quintet, J=7.6 Hz, 2 H), 2.05 (m, 1 H), 1.73 (m, 1 H), 0.91 (t, J=7.4 Hz, 3 h). $^{13}$C NMR (CDCl$_3$) δ 173.0, 166.1, 161.1, 156.3, 151.6, 117.2, 107.0, 53.1, 51.7, 49.8, 49.2, 34.5, 25.4, 20.7, 12.4. IR (neat) 1741, 1710, 1668 cm$^{-1}$.

EXAMPLE 18

14-Carbonethoxy-de-AB-deoxycamptothecin (8)

A mixture of ester 7 (5.01 g, 17.1 mmol), paraformaldehyde (3.08 g), concentrated H$_2$SO$_4$ (1 mL) and water (1 mL) in dioxane (25 mL) in a sealed thick wall tube was heated at 107° C. for 24 h. The resulting solution was then poured to brine (60 mL) and extracted with CH$_2$Cl$_2$ (4×50 mL). The combined extracts were dried (MgSO$_4$), filtered, and concentrated to a pale yellow oil which eventually solidified upon standing. $^1$H NMR (CDC$_3$) δ 5.48 (d, J=5.8 Hz, 1 H), 5.13 (d, J=5.8 Hz, 1 H), 4.34 (dd, J=5.1, 9.1 Hz, 1H), 4.19, (dt, J=2.9, 7.6 Hz, 2H), 3.85 (s, 3H), 3.48 (dt, J=3.6, 7.9 Hz, 2H), 2.22 (quintet, J=7.6 Hz, 2H), 1.65–2.01 (m, 2H), 1.08 (t, J=7.6 Hz, 3H). $^{13}$C NMR (CDCl$_3$) δ 171.3, 165.2, 157.9, 167.0, 147.3, 118.5, 104.9, 65.0, 52.0, 49.5, 44.3, 34.8, 25.3, 20.7, 11.9. IR (neat) 1734, 1713, 1650 cm$^{-1}$.

EXAMPLE 19

De-AB-deoxycamptothecin (9)

A mixture of tricycle 8 in aqueous HBr (48%, 50 mL) was heated in a sealed tube at 105° C. for 18 h. The resulting solution was then poured into brine (60 mL) and extracted with CH$_2$Cl2 (4×50 mL). The combined extracts were dried (MgSO$_4$), filtered, and concentrated. The residue was then subjected to flash chromatography (50/50/1 CHCl$_3$/EtOAc/MeOH) to afford 9 as an off-white solid (2.11 g, 53%), m.p. 146.0°–147.5° C. $^1$H NMR (CDCl$_3$) δ 5.98 (s, 1H), 5.38 (d, J=5.7 Hz, 1H), 5.20 (d, J=5.7 Hz, 1H), 4.12 (t, J=7.3 Hz, 2H), 3.35 (t, J=6.6 Hz, 1H), 3.08 (t, J=7.7 Hz, 2H), 2.21 (quintet, J=7.4 Hz, 2H), 1.80–19.8 (m, 2H), 0.99 (t, J=7.4 Hz, 3H). $^{13}$C NMR (CDCl$_3$) δ 171.4, 158.5, 150.5, 146.6, 117.2, 100.2, 66.1, 48.6, 45.8, 31.8, 25.1, 21.5, 11.3. IR (neat) 1739, 1651, 1574 cm$^{-1}$.

EXAMPLE 20

2-Hydroxy-de-AB-camptothecin (10)

A mixture of 9 (778 mg, 3.33 mmol) and SeO$_2$ (1.85 g, 16.7 mmol) in 20 mL of 95% dioxane were heated together in a sealed tube at 160° C. for 4 h. The solution was then poured into water and extracted with CH$_2$Cl$_2$ (4×30 mL). The combined extracts was dried (MgSO$_4$), filtered, and concentrated. The dark solid residue was then chromatographed (3:1 CHCl$_3$/acetone, 300 mL) then (30:20:1 CHCl$_3$/acetone/MeOH, 500 mL) to afford 10 as a yellow solid (377.4 mg, 43%). The diastereomeric ratio is about 1/1. $^1$NMR (DMSO-d$_6$ with 1 small drop of D$_2$O) δ 6.51 (DMSO-d$_6$ with 1 small drop of D2O) δ 6.51 (s, 1H) , 5.25, (dd, J=15.4, 19.0 Hz, 2H), 5.13 (t, J=7.0 Hz, 1H), 4.08 (m, 1H), 3.83 (m, 1H), 2.42 (m, 1H), 1.93 (m, 1H), 1.76 (m, 2H), 0.82 (t, J=7.1 Hz, 3H) . $^{13}$C NMR (DMSO-d$_6$) δ 172.59, 172.54, 156.87, 152.94, 152.90, 149.83, 149.78, 116.33, 97.37, 72.71, 72.09, 72.04, 71.94, 65.16, 59.68, 45.62, 31.25, 31.19, 30.30, 30.26, 7.66 ppm (21 peaks observed).

IR (KBr) 3392, 1741, 1652, 1570 cm$^{-1}$. HRMS calc'd for C$_{13}$H$_{15}$NO$_5$ (M+): 265. 0950. Found: 265. 0952.

EXAMPLE 21

2-Oxo-de-AB-camptothecin (11)

To the suspension of 10 (356.1 mg, 1.34 mmol) and 4 Å molecular sieves (activated powder, 1.50 g) in CH$_2$Cl$_2$ ( 15 mL) at 0° C. was added pyridinium dichromate (1.01 g, 2.68 mmol). After 3.5 h, 30 mL of EtOAc was added to the mixture, and the slurry was filtered through a plug of silica gel and celite. Evaporation of the filtrate and chromatography ( 1: 1 CHCl$_3$/EtOAc) gave 11 (159.6 mg, 45%). $^1$H NMR (CDCl$_3$) δ 7.23 (s, 1H), 5.68 (d, J=7.1 Hz, 1H), 5.25 (d, J=7.1 Hz, 1H), 4.35 (t, J=6.8 Hz, 2H), 3.65 (s, 1H), 2.97 (t, J=6.8 Hz, 2H), 1.82 (m, 2H), 0.99 (t, J=7.4 Hz, 3H). $^{13}$C NMR (CDCl$_3$) δ 196.0, 173.3,157.7,149.3,139.9,124.5, 100.8, 72.3, 66.3, 42.2, 33.7, 31.8, 7.7. IR (neat) 3404, 1736, 1656, 1598 cm$^{-1}$. HRMS calc'd for C$_{13}$H$_{13}$NO$_5$ (M+) 263.0794. Found: 263.0809.

EXAMPLE 21 dl-Camptothecin (11)

A suspension of 11 (185.2 mg, 0.704 mmol) and amino toluidine 14 (Chem. Ber., 76, 1099 (1943); 178 mg, 0.844 mmol) in toluene (20 mL) was refluxed for 0.5 h. Then, p-TsOH (10 mg) was added, and the reaction was refluxed with a Dean-Stark trap for 3.5 h. The solution was cooled to room temperature and solvent was removed. Column chromatography (100:10:1 CHCl$_3$/MeCH/MeOH) gave 196.5 mg (80%) of 1 as a tan solid. Recrystallization (10% MeOH/CHCl$_3$) gave 173.1 mg of 1 as an off-white solid, mp 264°–265° C. (dec). $^1$H NMR (DMSO-d$_6$) δ 8.70 (s, 1H), 8.16 (m, 2H), 7.88 (t, J=7.5 Hz, 1H), 7.72 (t, J=7.3 Hz, 1H), 7.36 (s, 1H), 6.54 (s, 1H), 5.43 (s, 2H), 5.30 (s, 1H), 1.87 (m, 2H), 0.88 (t, J=7.0 Hz). $^{13}$C NMR (CDCl$_3$) δ 172.4, 156.8, 149.9, 147.9, 145.4, 131.6, 130.3, 129.8, 129.0, 128.4, 127.9, 127.6, 119.0, 96.6, 72.3, 65.2, 50.2, 30.2, 7.7 ppm (19 peaks observed). IR (KBr) 3271, 1755, 1651, 1583 cm$^{-1}$. HRMS calc'd for C$_{20}$H$_{16}$N$_2$O$_4$ (M+1$^1$): 349.1188. Found: 349.1184.

EXAMPLE 22

14-Carbomethoxy-2-hydroxy-de-AB-deoxycamptothecin (15)

To an oxygenated solution of 10 (291 mg, 1.00 mmol) and 0.38 mL (2.20 mmol) of P(OEt)$_3$ in 20 mL of THF at −70° C. was added NaHMDS (1.1 mL, 1.1 mmol) over 2 min. The solution was warmed to room temperature over 7 h and was quenched with saturated NH$_4$Cl (10 mL) . The reaction mixture was extracted with CHCl$_3$ (30 mL×3) and the extracts were dried (MgSO$_4$), filtered, and concentrated. The residue was then loaded to a flash column, eluted with 9:1 CHCl$_3$/MeOH to give alcohol 15 (230 mg, 75%) as a mixture of diastereomers (1.3:1 ratio from integration of $^1$H NMR). $^1$H NMR (CDCl$_3$) δ 5.40–5.52 (m, 3H) , 5.10 (m, 2H), 4.42 & 4.05 (1H), 4.24 (m, 2H), 3.90 (s, 3H), 2.31 (m, 2H), 1.70–1.91 (m, 2H), 1.09 & 0.98 (2 t's, J=7.3 Hz, 3H). IR (neat) 3390, 2958, 1732, 1651 cm$^{-1}$. HRMS calc'd for C$_{15}$H$_{17}$NO$_6$ (M+): 307.1056. Found: 307.1062.

EXAMPLE 23

14-Carbomethoxy-2-oxo-de-AB-deoxycamptothecin (16)

A mixture of alcohol 15 (595 mg, 1.94 mmol), PDC (2.18 g, 5.80 mmol) and activated 4 A molecule sieve powder (2.20 g) in $CH_2Cl_2$ (20 mL) was stirred at 0°–5° C. for 4 h. It was then diluted with EtOAc (30 mL) and filtered through celite. The flask and the residue was rinsed and washed with 1:1 EtOAc/$CHCl_3$ (20 mL×5) and the filtrate was concentrated to give pure 16 (490.2 rag, 83%). $^1H$ NMR ($CDCl_3$) δ 5.55 (d, J=17.2 Hz, 1H), 5.24 (d, J=17.2 Hz, 1H), 4.32 (t, J=6.8 Hz, 2H), 3.93 (s, 3H), 3.68 (dd, J=5.2, 8.6 Hz, 1H), 2.97 (t, J=6.8 Hz, 2H), 2.01 (m, 1H), 1.80 (m, 1H), 1.04 (t, J=7.4 Hz, 3H). $^{13}C$ NMR ($CDCl_3$) δ 194.3, 169.5, 157.2, 144.6, 137.7, 126.4, 110.2, 65.7, 53.4, 43.6, 42.2, 33.7, 26.1, 11.5. IR (neat) 1742, 1658 $cm^1$. HRMS calc'd for $C_{15}H_{15}NO_6$ (M+): 305.0899. Found: 305.0911.

EXAMPLE 24

Benzylidene (17)

To a solution of 587 mg (2.0 mmol) of ester 10 and 0.19 mL (1.9 mmol) of benzaldehYde in 15 mL of THF at −70° C. was added 2.2 mL (2.2 mmol) of NaHMDS (1M in THF). The orange solution was allowed to warm to room temperature over 16 h before it was quenched with 15 mL of 5% HCl. After an additional 2 h, the mixture was extracted with 4:1 $CHCl_3$/MeOH (5×20 mL), dried ($MgSO_4$) and concentrated. The resulting yellow solid was triturated with THF to afford 624 mg (90%) of 17 as a white solid. $^1H$ NMR ($CDCl_3$) δ 7.21 (m, 6H), 5.32, (d, J=16.1 Hz, 1H), 5.01 (d, J=16.1 Hz, 1H), 3.98 (t, J=7.4 Hz, 2H), 3.63 (m, 1H), 3.04 (dt, J=2.3, 6.2 Hz, 2H), 1.88 (m, 1H), 1.68 (m, 1H), 0.89 (t, J=7.4 Hz, 3H). $^{13}C$ NMR ($CDCl_3$/$CD_3OD$) δ 171.4, 167.1, 157.6, 146.9, 145.4, 135.4, 132.5, 132.5, 128.8, 117.9, 107.9, 65.4, 46.6, 44.3, 27.7, 25.4, 11.4. IR ($CHCl_3$) 3500–2400, 1739, 1717, 1622, 1574, 1531, 1214, $cm^{-1}$. HRMS calc'd for $C_{21}H_{19}NO_5$ (M+): 365.1302. Found: 365.1311.

EXAMPLE 25

Keto acid (18)

A −70° C. solution of 7.0 mg (0.020 mmol) of 17 in 10 mL of MeOH and 10 mL of $CH_2Cl_2$ was subjected to $O_3$ for 10 rain before the addition of $Me_2S$. The mixture was allowed to warm to room temperature over 12 h then evaporated to leave 5.6 mg (96%) of ketone 18 which was used without further purification. $^1H$ NMR (DMSO-$d_6$/$CDCl_3$) δ 5.58 (d, J=17.2 Hz, 1H), 5.21 (d, J=17.2 Hz, 1H), 4.29 (t, J=7.2 Hz, 2H), 3.80 (m, 1H), 2.97 (t, J=7.2 Hz, 2H), 2.11, (m, 1H), 1.84 (m, 1H), 0.91 (t, J=7.2 Hz, 3H). IR (neat) 3426, 1738, 1712. 1659 $cm^{-1}$.

EXAMPLE 26

14-Carbomethoxy-2-oxo-de-AB-deoxycamptothecin (16)

A solution of 291 mg (1.0 mmol) of keto acid 17 in 3 mL of benzene and 1 mL of MeOH was treated with 0.65 mL of $TMSCHN_2$ (2M in hexane) . After stirring for 3h the solvents were evaporated and the residue was chromatographed (95:5 $CHCl_3$/MeOH) to afford 287 mg (94%) of ester 16. $^1H$ NMR ($CDCl_3$) δ 5.55 (d, J=17.2 Hz, 1H) , 5.24 (d, J=17.2 Hz, 1H), 4.32 (t, J=6.8 Hz, 2H), 3.93 (s, 3H), 3.68 (dd, J=5.2, 8.6 Hz, 1H), 2.97 (t, J=6.8 Hz, 2H), 2.01 (m, 1H), 1.80 (m, 1H), 1.04 (t, J=7.4 Hz, 3H). $^{13}C$ NMR ($CDCl_3$) δ 194.3m, 169.5, 164.0, 157.2, 144.6, 137.7, 126.4, 110.2, 65.7, 53.4, 43.6, 42.2, 33.7, 26.1, 11.5. IR (neat) 1742, 1658 $cm^{-1}$.

EXAMPLE 27

14-Carbomethoxy-20-deoxycamptothecin (19)

A solution of keto ester 16 (601 mg, 1.97 mmol) and amine 14 (*Chem. Ber.*, 76, 1099 (1943); 497 mg, 2.36 mmol) in toluene (20 mL) was refluxed for 40 min. TsOH (20 mg) was added, the reaction flask was equipped with a Dean-Stark trap, and the whole was refluxed for 4 h before the reaction was cooled to room temperature. The mixture was concentrated (10 mL) and the resulting solid was filtered and recrystallized ($CHCl_3$) to give 19 (578 mg, 75%), mp 300°–302° C. (dec.) $^1H$ NMR ($CDCl_3$) δ 8.38 (s, 1H), 8.11 (d, J=8.4 Hz, 1H), 7.91 (d, J=8.2 Hz, 1H), 7.81 (dt, J=1.2, 7.7 Hz, 1H), 7.66 (t, J=7.5 Hz, 1H), 5.62 (d, J=16.2 Hz, 1H), 5.30 (d, J=16.2 hz, 1H), 5.28 (s, 2H, 4.12 (s, 3H), 3.78 (dd, J=5.2, 8.7 Hz, 1H), 2.12 (m, 1H), 1.93 (m, 1H), 1.11 (t, J=7.4 Hz, 3H). $^{13}C$ NMR ($CDCl_3$) δ 170.2, 165.6, 157.2, 151.4, 148.8, 145.1, 144.4, 130.9, 130.6, 130.3, 128.53, 128.48, 128.04, 127.99, 120.5, 108.3, 65.7, 52.9, 50.2, 44.1, 26.0, 11.6. IR (KBr) 2930, 1732, 1652, 1616, 1452 $cm^{-1}$. HRMS calc'd for $C_{22}H_{18}N_2O_5$ (M+): 390.1216. Found: 390.1231.

EXAMPLE 28

20-Desoxycampothecin (20)

A solution of ester 19 (207.5 mg, 0.531 mmol) in 48% aqueous HBr (8 mL) in sealed tube was heated for 15 h at 140° C. After it was cooled, the reaction mixture was concentrated to near dryness via vacuum. The mixture was then carefully neutralized with 2N NaOH and saturated $NaHCO_3$ to pH 7.5. The aqueous mixture was extracted with $CHl_3$ (15 mL×10) and the combined extracts were dried ($MgSO_4$), filtered, and concentrated. The residue was flash chromatographed (49:1 $CHCl_3$/MeOH) to give 20 (124.3 mg, 71%). $^1H$ NMR (400 MHz, $CDCl_3$) δ 8.39, (s, 1H), 8.21 (d, J=8.4 Hz, 1H), 7.93 (d, J=7.0 Hz, 1H), 7.83 (dt, J=1.4, 16.9 Hz, 1H), 7.66 (dt, J=1.0, 7.5 Hz, 1H), 7.19 (s, 1H), 5,57 (d, J=16.3 Hz, 1H), 5.39 (d, J=16.3 Hz, 1H), 5.29 (s, 2H), 3.62 (t, J=6.6 Hz, 1H), 2.09 (m, 2H), 1.09 (t, J=7.4 Hz, 3H). $^{13}C$ NMR (100 MHz, $CDCl_3$) δ 170.9, 157.9, 152.4, 148.9, 147.2, 146.0, 131.2, 130.7, 129.7, 128.6, 128.2, 128.1, 120.7, 99.8, 66.1, 50.0, 45.9, 25.4, 11.4.HMRS clac'd for $C_{20}H_{16}N_2O_3$ (M+): 332.1161. Found: 332.1151.

EXAMPLE 29 dl-Camptothecin (1)

To a solution of 20 (47.8 mg, 0.144 mmol), $CuCl_2$ (80 mg) and diethylamine (100 μl ) in DMF (16 mL) was bubbled in oxygen for 7 h. The reaction mixture was concentrated in vacuo to about 5 mL, and was then diluted with water. A solution of saturated $NH_4Cl$ was used to adjusted the pH to 6, and the resulting mixture was extracted with chloroform (10×10mL). The combined extracts were dried ($MgSO_4$) filtered, and concentrated. The residue was flash chromatographed (98: 2 $CHCl_3$/MeOH) to give 1 (45.5 mg, 91%).

EXAMPLE 30

14-Carbomethoxy-10-methoxy-20-deoxycamptothecin (22)

A solution of amino acetal 21 (*J. Med. Chem.*, 23, 554 (1980); 329 mg., 1.69 mmol) and ketone 16 (429 mg, 1.41 mmol) in 15 mL of toluene were heated together for 30 min before the addition of 10 mg of p-TsOH. The resulting red solution was heated at reflux with removal of water for 3.5 h. The solvent was removed and the residue was chromatographed (99:1 $CHCl_3$/MeOH) then triturated with a 2:1 ether/THF solution to afford 444 mg (75%) of ester 22 as an off-white solid. $^1H$ NMR ($CDCl_3$) δ 8.24 (s, 1H), 7.99 (d, J=9.3 Hz, 1H), 7.44 (dd, J=2.8, 9.3 Hz, 1H), 7.13 (d, J=2.7, 1H), 5.61 (d, J=16.3 Hz, 1H), 5.29 (d, J=16.2 Hz, 1H), 5.24 (s, 2H), 4.15 (s, 3H), 3.97 (s, 3H), 3.85 (m, 1H), 2.13 (m, 1H), 1.88 (m, 1H), 1.10 (t, J=7.5 Hz, 3H). $^{13}C$ NMR ($CDCl_3$) δ 170.3, 165.7, 159.3, 157.1, 145.0, 144.9, 131.6, 129.4, 129.1, 123.7, 119.6, 105.0, 65.6, 55.7, 52.8, 50.1, 43.9, 25.9, 11.5. IR (KBr) 1731, 1651 $cm^{-1}$. HRMS calc'd for $C_{23}H_{21}N_2O_6$ (M30 H): 421.1477. Found: 42 1.1421.

EXAMPLE 31

10-Hydroxycamptothecin (24)

A solution containing 24.1 mg (0,057 mmol) of ester 22 in 2 mL of 48% HBr was heated at 140° C. in a sealed tube for 15 h. The solvent was evaporated and the residue was made neutral by the addition of sat'd $NaHCO_3$ solution. The aqueous solution was extracted with 4:1 $CHCl_3$/MeOH (5×10 mL) and dried ($MgSO_4$). Evaporation of the solvent gave crude 10-hydroxy-20-deoxycamptothecin (23) which was immediately dissolved in 2 mL of DMF. After the addition of $CuCl_2$ (40 mg) and $Me_2NH$ (50 μL), O2 was passed through the solution for 8 h. The mixture was then diluted with water (3 mL) and sat'd $NH_4Cl$ was added to adjust the pH to 6. Extraction with $CHCl_3$ (5×10 mL), drying ($MgSO_4$), chromatography (9:1 $CHCl_3$/MeOH), and recyrstallization (13% MeOH/$CHCl_3$ and EtOAc) afforded 17.3 mg (83%) of mp 266°–268° C. (lit. [*J. Med. Chem.*, 23, 554 (1980)] 265°–268° C.).

EXAMPLE 32

Benzylic alcohol (26)

To a 70° C. solution of 860 mg (4.75 mmol) of 5-methoxy-2-nitrobenzaldehyde (25) in 20 mL of THF was added 6.65 mL (6.65 mmol) of vinylmagnesium bromide. After stirring for 3.5 h, the mixture was quenched with 20 mL of 0.010N HCl and diluted with 100 mL of ether (3×25 mL). The yellow extracts were dried ($MgSO_4$) and concentrated to afford 993 mg (100%) of alcohol 26. $^1H$ NMR ($CDCl_3$) δ 7.95 (d, J=9.1 Hz, 1H), 7.19 (d, J=2.8 Hz, 1H), 6.70 (dd, J=2.8, 9.1 Hz, 1H), 5.96 (m, 1H), 5.84 (d, J=5.2 Hz, 1H), 5.30 (dt, J=1.3, 17.5, Hz, 1H), 3.84 (s, 3H), 3.40 (bs, 1H). $^{13}C$ NMR ($CDCl_3$) δ 163.8, 141.4, 140.6, 138.0, 127.5, 115.8,113.1 (2 lines), 69.7, 55.8. IR (neat) 3437, 1613 $cm^{-1}$. HRMS calc'd for $C_{10}H_{11}NO_4$ (M+): 209.0727. Found: 209.0699.

EXAMPLE 33

Enone (27)

Freshly prepared Jones reagent (1.1 mL, 2.67M) was added dropwise to 418 mg (2.0 mmol) of alcohol 26 in 4 mL of acetone at room temperature. After 10 min, ice water (5 mL) was added followed by 1 ml of sat'd NaHSO]. The resulting mixture was extracted with ether (4×10 mL) then filtered through Florisil. Evaporation of the solvent left 363 mg (88%) of ketone 27 as an off-colored oil. $^1H$ NMR ($CDCl_3$) δ 8.08 (d, J=9.1 Hz, 1H), 6.99 (dd, J=2.8, 9.0 Hz, 1H), 6.75 (d, J=2.8 Hz, 1H), 6.59 (m, 1H), 5.97 (d, J=10.6 Hz, 1H), 5.78 (d, J=11.6 Hz, 1H), 3.85 (s, 3H). $^{13}C$ NMR ($CDCl_3$) δ 193.3, 164.1, 139.2, 138.1, 136.5, 130.9, 126.9, 115.3, 113.4, 56.2. IR (neat) 1681 $cm^{-1}$. HRMS calcd for $C_{10}H_9NO_4$ (M+): 207.0571. Found: 207.0535.

EXAMPLE 34

5-Methoxy-2-aminopropiophenone (28)

A solution of 207 mg (1.0 mmol) of nitro enone 27 in 3 mL of abs EtOH containing 10 mg of 10% Pd(C) was stirred under an atmosphere of $H_2$ for 4 h. After this time, the mixture was filtered through Celite and the solvent was evaporated to afford pure amino ketone 28 as a white solid, mp 57°–58° C. (lit. [*Helv. Chem. Acta*, 37, 1805 (1954)] mp 58° C.). $^1H$ NMR ($CDCl_3$) δ 7.25 (d, J=1.2 Hz, 1H), 6.96 (dd, J=1.2, 8.9 Hz, 1H), 6.63 (d, J=9.6 Hz, 1H), 3.77 (s, 3H), 2.96 (q, J=7.2 Hz, 2H), 1.60 (bs, 2H), 1.22 (t, J=7.2 Hz, 3H). $^{13}C$ NMR ($CDCl_3$) δ 203.5, 150.2, 144.7, 122.7, 118.7, 117.9, 113.9, 56.0, 32.4, 8.6. IR (neat) 3469, 3352, 1659 $cm^{-1}$.

EXAMPLE 35

14-Carbomethoxy-7-ethyl-10-methoxy-20-deoxycamptothecin (29)

A solution of amino ketone 28 (179 mg., 1.00 mmol) and tricyclic ketone 17 (244 mg, 0,800 mmol) in 10 mL of toluene were heated together for 30 min before the addition of 10 mg of p-TsOH. The resulting red solution was heated at reflux with removal of water of 7.25 h. The solvent was removed and the residue was chromatographed (9:1 $CHCl_3$/MeOH) then triturated with 2:1 ether/THF solution to afford 283 mg (79%) of ester 29 as an off-white solid. $^1H$ NMR ($CDCl_3$) δ 8.02 (d, J=9.2 Hz, 1H), 7.45 (dd, J=2.7, 9.2 Hz, 1H), 7.29 (d, J=2.7 Hz, 1H), 5.64 (dd, J=16.3 Hz, 1H), 5.31 (d, J=16.3 Hz, 1H), 5.22 (s, 2H), 4.11 (s, 3H), 4.02 (s, 3H), 3.79 (m, 1H), 3.15 (q, J=7.7 Hz, 2H), 2.10 (m, 1H), 1.94 (m, 1H), 1.38 (t, J=7.7 Hz, 3H), 1.11 (t, J=7.5 Hz, 3H). $^{13}C$ NMR ($CDCl_3$) δ 170.3, 165.7, 159.2, 157.3, 148.4, 145.8, 145.4, 145.1, 143.4, 132.6, 128.1, 127.2, 122.6, 119.4, 101.2, 65.6, 55.7, 52.8, 49.5, 44.0, 25.9, 23.1, 13.5, 11.6. HRMS calc'd for $C_{25}H_{25}N_2O_6$ (M+H): 448.9835. Found: 448.9818.

EXAMPLE 36

7-Ethyl-10-hydroxycamptothecin (31)

A solution containing 44.8 mg (0.10 mmol) of ester 29 in 5 mL of 48% HBr was heated at 140° C. in a sealed tube for 15 h. The solvent was evaporated and the residue was made neutral by the addition of sat'd $NaHCO_3$ solution. The aqueous solution was extracted with 4:1 $CHCl_3$/MeOH (5×10 mL) and dried (MgSO4). Evaporation of the solvent gave crude 7-ethyl-10-hydroxy-20-deoxycamptothecin (30) which was immediately dissolved in 4 mL of DMF. After the addition of CuCl2 (80 mg) and $Me_2NH$ (100 μL), O2 was passed through the solution for 8 h. The mixture was then diluted with water (10 mL) and sat'd $NH_4Cl$ was added to adjust the pH to 6. Extraction with $CHCl_3$ (5×15 mL), drying ($MgSO_4$) and chromatography (9:1 $CHCl_3$/MeOH) afforded 17.3 mg (83%) of 31. This material had spectroscopic properties (¹HNMR and IR) identical to the previously reported (+)-isomer, mp 214°–217° C. (lit. [*Chem. Pharm. Bull.*, 39, 1446 (1991)] mp 214° C.).

What is claimed is:

1. A process of synthesizing a compound having the structure:

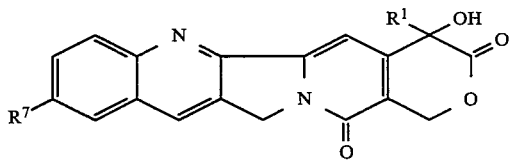

wherein R¹ is ethyl and R⁷ is OH, which comprises:

(a) condensing a compound having the structure:

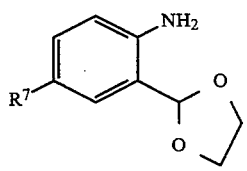

wherein R⁷ is OH with a compound having the structure:

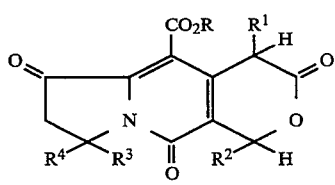

wherein R is H, or a linear or branched chain alkyl, alkylaryl, or hydroxyalkyl group, or an aryl group; R¹ is ethyl; R², R³, and R⁴ are H; and, R⁷ is OR with a suitable acidic catalyst comprising p-toluenesulfonic acid in toluene to form a compound having the structure:

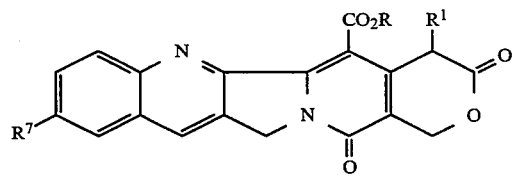

wherein R is H, or a linear or branched chain alkyl, alkylaryl, or hydroxyalkyl group, or an aryl group; R¹ is ethyl; and, R⁷ is OR;

(b) hydrolyzing and decarboxylating the compound formed in step (a) with a suitable acid comprising hydrobromic acid to form a compound having the structure:

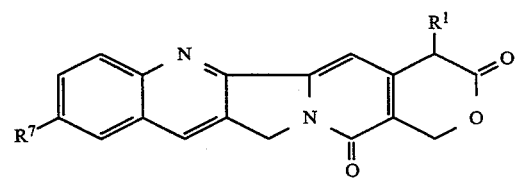

wherein R¹ is ethyl and R⁷ is OR; and, (c) treating the compound formed in step (b) with a hydroxylating reagent under suitable conditions to form a compound having the structure:

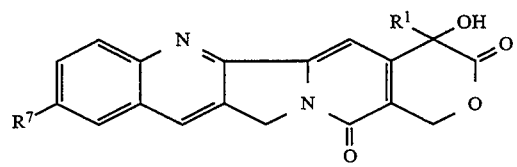

wherein R¹ is ethyl and R⁷ is OH.

2. The process of claim 1, wherein the hydroxylating reagent of the treating step (c) comprises gaseous oxygen, cupric halide, and a base.

3. A process of synthesizing a compound having the structure:

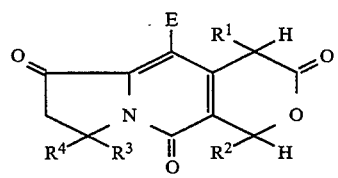

wherein E is H, CO₂R, CONH₂, CONHR, CONR₂, or CN; R¹ R², R³, and R⁴ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) treating a compound having the structure:

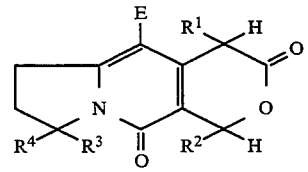

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, with a hydroxylating reagent under suitable conditions to form a compound having the structure:

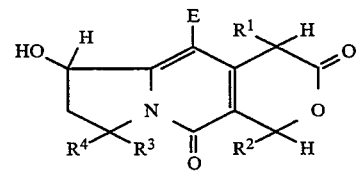

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) oxidizing the compound formed by step (a) with an oxidant under suitable conditions to form a compound having the structure:

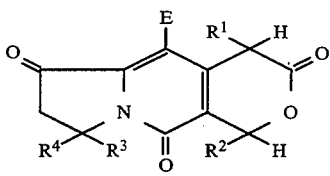

wherein E is H, CO₂R, CONH₂, CONHR, CONR₂, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group.

4. The process of claim 3, wherein the hydroxylating reagent of the treating step (a) comprises gaseous oxygen, trialkyl phosphite, and sodium hexamethyldisilazide.

5. The process of claim 3, wherein the oxidant is pyridinium dichromate.

6. A process of synthesizing a compound having the structure:

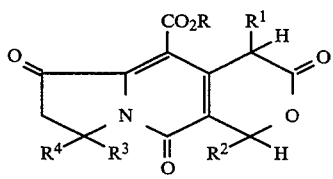

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) condensing an aryl aldehyde with a compound having the structure:

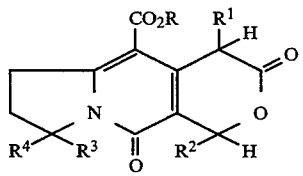

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, with a basic reagent under suitable conditions to form a compound having the structure:

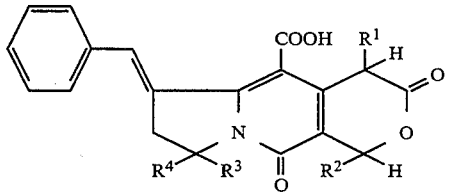

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) ozonolyzing the compound formed by step (a) under suitable conditions to form a compound having the structure:

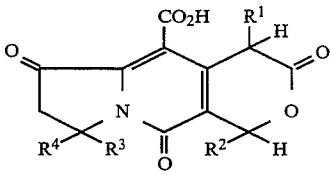

wherein $R^1$, $R^2$, $R^3$, and $R^4$ are independently the same or different and are H, or a linear or branched chain alkyl, alkylaryl, or hydroxyalkyl group, or an aryl group; and, (c) re-esterifying the compound formed in step (b) with a suitable reagent under suitable conditions to form a compound having the structure:

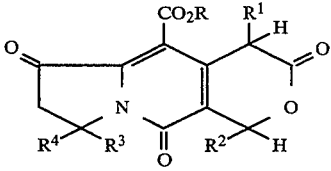

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group.

7. The process of claim 6, wherein the basic reagent of the condensing step (a) comprises sodium hexamethyldisilazide.

8. The process of claim 6, wherein the reagent of reesterifying step (c) is trimethylsilyldiazomethane.

9. A process of synthesizing a compound having the structure:

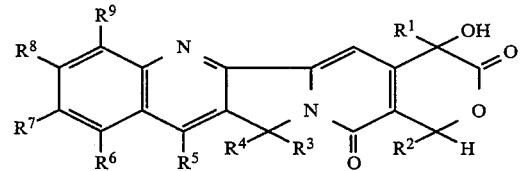

wherein $R^1$, $R^2$, $R^8$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, which comprises:

(a) preparing in accord with claim 3 or 6 a compound having the structure:

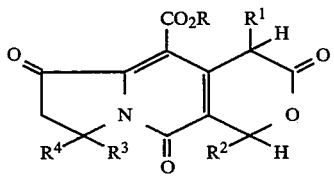

wherein R is H, or a linear or branched chain alkyl, alkylaryl, or hydroxyalkyl group, or an aryl group; $R^1$, $R^2$, $R^3$, and $R^4$ are independently the same or different and are H, or a linear or branched chain alkyl, alkylaryl, or hydroxyalkyl group, or an aryl group;

(b) condensing the compound formed in step (a) with a compound having the structure:

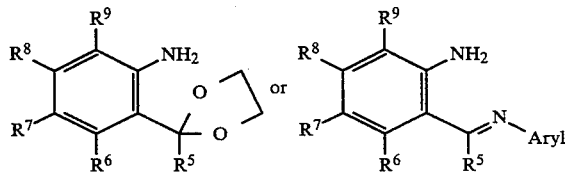

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, under suitable conditions to form the compound having the structure:

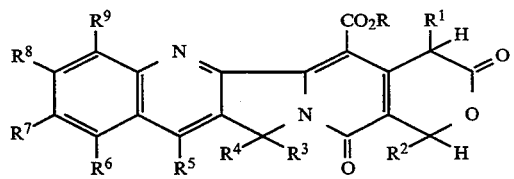

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group or an aryl group; and, n is an integer from 0 to 9;

(c) hydrolyzing and decarboxylating the compound formed in step (b) under suitable conditions to form a compound having the structure:

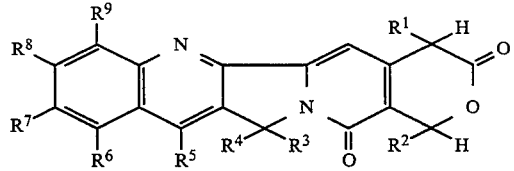

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9; and, (d) treating the compound formed in step (c) with a hydroxylating reagent under suitable conditions to form a compound having the structure:

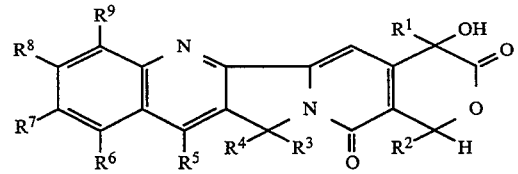

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9.

10. A process of synthesizing a compound having the structure:

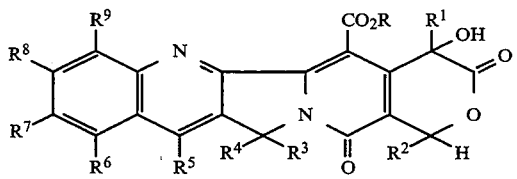

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, which comprises:

(a) preparing in accord with claim 9 a compound having the structure:

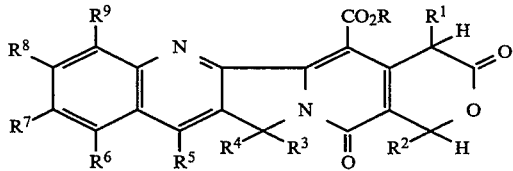

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9; and, (b) treating the compound formed in step (a) with a hydroxylating reagent under suitable conditions to form a compound having the structure:

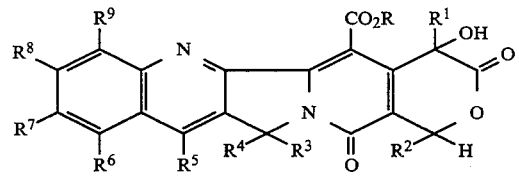

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9.

11. The process of claims 9 and 10, wherein the hydroxylating reagent in step (d) of claim 9 and in step (b) of claim 10, respectively, comprises gaseous oxygen, cupric halide, and a base.

* * * * *